US010022307B2

(12) United States Patent
Chisholm et al.

(10) Patent No.: US 10,022,307 B2
(45) Date of Patent: Jul. 17, 2018

(54) HARDENABLE TWO PART ACRYLIC COMPOSITION

(71) Applicant: Lucite International UK Limited, Southampton, Hampshire (GB)

(72) Inventors: Michael Stephen Chisholm, Newton Aycliffe (GB); David McDonald, Newton Aycliffe (GB); Sera Saheb Abed-Ali, Newton Aycliffe (GB); Ian Robinson, Guisborough (GB)

(73) Assignee: LUCITE INTERNATIONAL SPECIALITY POLYMERS AND RESINS LIMITED, Southampton (GB)

( * ) Notice: Subject to any disclaimer, the term of this patent is extended or adjusted under 35 U.S.C. 154(b) by 873 days.

(21) Appl. No.: 14/386,555

(22) PCT Filed: Mar. 21, 2013

(86) PCT No.: PCT/GB2013/050744
§ 371 (c)(1),
(2) Date: Sep. 19, 2014

(87) PCT Pub. No.: WO2013/144590
PCT Pub. Date: Oct. 3, 2013

(65) Prior Publication Data
US 2015/0051603 A1 Feb. 19, 2015

(30) Foreign Application Priority Data

Mar. 30, 2012 (GB) .................................. 1205677.6

(51) Int. Cl.
| | | |
|---|---|---|
| *A61K 6/08* | (2006.01) | |
| *A61B 17/88* | (2006.01) | |
| *A61K 6/00* | (2006.01) | |
| *A61K 6/02* | (2006.01) | |
| *C04B 26/06* | (2006.01) | |
| *C08F 285/00* | (2006.01) | |
| *C08F 265/06* | (2006.01) | |
| *A61K 6/083* | (2006.01) | |
| *C08L 33/12* | (2006.01) | |
| *C04B 111/00* | (2006.01) | |

(52) U.S. Cl.
CPC ........ *A61K 6/0835* (2013.01); *A61B 17/8825* (2013.01); *A61K 6/005* (2013.01); *A61K 6/0017* (2013.01); *A61K 6/0079* (2013.01); *A61K 6/024* (2013.01); *C04B 26/06* (2013.01); *C08F 265/06* (2013.01); *C08F 285/00* (2013.01); *C08L 33/12* (2013.01); *C04B 2111/00836* (2013.01)

(58) Field of Classification Search
CPC .... A61K 6/0835; A61K 6/0017; A61K 6/005; A61K 6/0079; A61K 6/024; A61B 17/8825; C04B 26/06; C04B 2111/00836; C08F 265/06; C08F 285/00; C08L 33/12
USPC ........................................................... 606/94
See application file for complete search history.

(56) References Cited

U.S. PATENT DOCUMENTS

| | | |
|---|---|---|
| 4,093,576 A | 6/1978 | deWijn |
| 4,268,639 A | 5/1981 | Seidel et al. |
| 5,258,420 A | 11/1993 | Posey-Dowty et al. |
| 5,650,108 A | 7/1997 | Nies et al. |
| 5,902,839 A | 5/1999 | Lautenschlager et al. |
| 6,409,972 B1 | 6/2002 | Chan |
| 2007/0032567 A1 | 2/2007 | Beyar et al. |
| 2007/0116734 A1* | 5/2007 | Akash ................. A61F 2/30 424/423 |
| 2007/0213425 A1 | 9/2007 | Higham et al. |
| 2009/0239970 A1 | 9/2009 | Rodrigues et al. |
| 2010/0210784 A1 | 8/2010 | Schmitt et al. |
| 2010/0286331 A1 | 11/2010 | Schmitt et al. |

(Continued)

FOREIGN PATENT DOCUMENTS

| | | | |
|---|---|---|---|
| EP | 0009754 A1 | 4/1980 | |
| GB | WO 2010018412 A1 * | 2/2010 | ............ C08F 265/04 |
| JP | 2010-522591 A | 7/2010 | |

(Continued)

OTHER PUBLICATIONS

Methyl Methacrylate—https://cameochemicals.noaa.gov/chris/MMM.pdf—Online Jun. 17, 1999 Downloaded—Nov. 20, 2017.*

(Continued)

*Primary Examiner* — Ling Siu Choi
*Assistant Examiner* — Ronald Grinsted
(74) *Attorney, Agent, or Firm* — Shumaker, Loop & Kendrick, LLP

(57) ABSTRACT

A hardenable two part acrylic composition is described for the treatment of human or animal bone is described. The composition comprises a storage stable liquid first part and a storage stable liquid second part which react with each other upon mixing to form a cement which hardens. The composition further comprises an acrylic monomer component and an initiator component in an amount effective to polymerize the monomer component. The monomer component and the initiator component are generally located in separate parts of the two part composition so that the monomer component is storage stable. The liquid first part comprises emulsion polymerized acrylic polymer particles in a liquid carrier. A method of producing a hardenable two part acrylic composition is also described. The composition is particularly useful in a syringe or caulking gun having at least two barrels.

30 Claims, No Drawings

(56) References Cited

U.S. PATENT DOCUMENTS

2011/0054392 A1 3/2011 Nies
2011/0263739 A1 10/2011 Chisholm

FOREIGN PATENT DOCUMENTS

| JP | 2011-530641 A | 12/2011 |
|---|---|---|
| RU | 2128523 C1 | 4/1999 |
| WO | 2004/071543 A1 | 8/2004 |
| WO | 2008/116905 A2 | 10/2008 |
| WO | 2009007253 A1 | 1/2009 |
| WO | 2009007254 A1 | 1/2009 |
| WO | 2009007255 A1 | 1/2009 |
| WO | 2010/005442 A1 | 1/2010 |
| WO | WO2010/018412 A1 | 2/2010 |

OTHER PUBLICATIONS

International Search Report for International Application No. PCT/GB2013/050744 dated Jul. 16, 2013; 4 pages.
International Preliminary Report on Patentability issued by the International Bureau of WIPO dated Oct. 1, 2014 for International Application PCT/GB2013/050744.
Search Report issued by the UK Patent Office dated Feb. 26, 2013 for GB1205677.6.
Lewis, Gladius and Carroll, Michael; Rheological properties of acrylic bone cement during during and the role of the size of the powder particles; Journal of Biomedical Materials Research; J. Biomed. Mater. Res., 63: 191-199.
McCabe, J.F., Spence, D. and Wilson, H.J.; Doughing time of heat-cured dental acrylic resins and its dependence on polymer particle size distribution; Journal of Oral Rehabilitation, 2: 199-207.
de Wijn, J.R. (1976), Poly(methyl methacrylate)-aqueous phase blends; In situ curing pours materals; Journal of Biomedical Materials Research, 10: 625-635.
Boger, et al.; Properties of an Injectable Low Modulus PMMA Bone Cement for Osteoporotic Bone; Journal of Biomedical Materials Resource Part B: Applied Biomaterials; vol. 86B, Part 2, pp. 474-482 (2008).
Hasenwinkel, et al.; Effect of initiation chemistry on the fracture toughness, fatigue strength, and residual monomer content of a novel high-viscosity, two-solution acrylic bone cement; Journal of Biomedical Materials Research; vol. 47, No. 1, 1999, pp. 36-45.

* cited by examiner

HARDENABLE TWO PART ACRYLIC COMPOSITION

The present invention relates to a polymer composition, in particular but not exclusively, a two part acrylic composition which reacts upon mixing of the two parts to form a cement which hardens to a solid, a twin barreled syringe or caulking gun accommodating the two part composition and a method of producing the two part composition.

Hardenable compositions formed by mixing together acrylic polymers and monomers are useful in a wide range of applications. Particular utility is found in dental, medical, adhesive and construction applications, where such materials have been used for over 40 years.

Dental applications include their use in denture bases, denture base plates, denture liners, denture repairs, custom trays, veneering for crowns and bridgework, artificial teeth, veneers and repair for natural teeth and tooth restorative fillings.

Medical applications include their use as bone cements. Bone cements find applications generally in the filling of bone cavities and in particular, as prosthetic cements, cranial cements, vertebral cements in vertebroplasty and kyphoplasty and in the production of shaped articles that harden extra-corporeally and which can then be introduced into the body.

Adhesive and construction applications include numerous applications such as their use in jointing, cementing, gap filling, sealing, laminating and in the formation of porous materials.

Hardenable acrylic compositions are generally composed of a solid component and liquid component. The solid component comprises a powder formed from polymer particles and, if appropriate, further additives, such as polymerization initiators and catalysts, fillers, pigments and dyestuffs. The liquid component comprises a liquid monomer or monomers and further additives, such as accelerators and stabilisers. When ready for use, the solid and liquid components are mixed together to form a liquid or semi-solid paste, which, under the action of the polymerization initiators and accelerators, increases in viscosity and hardens into a solid.

The solid component typically used consists of small spherical beads (usually about 20-150 microns in diameter) of poly(methyl methacrylate) (PMMA) and a small amount of polymerization initiator such as dibenzoyl peroxide (BPO), usually encapsulated within the PMMA bead, but which can also be added as a separate component. The liquid component is usually a monomer, typically methyl methacrylate (MMA), which may also contain a polymerization activator such as N,N-dimethyl-p-toluidine (a tertiary amine) (DMPT) and an inhibitor such as hydroquinone (HQ) to prevent the monomer from spontaneously polymerizing.

When the solid and liquid components are mixed together, the polymer particles are wetted with monomer, solvated and begin to dissolve. The solvated polymer particles release dibenzoyl peroxide initiator into the monomer which interacts with activator, if present, to produce radicals that react with the monomer and initiate room temperature addition polymerization of the monomer. The mixture starts out at a relatively low viscosity and progresses to a stiffer and stiffer system that eventually hardens completely.

This constantly changing viscosity of the mixture is characterised by dough and set times and maximum exotherm temperature attained, as defined by BS ISO 5833: 2002. The dough time is considered to be the length of time following the start of mixing for the mixture to achieve a dough-like mass that does not adhere to a gloved finger when gently touched. The set time is considered to be the time taken to reach a temperature midway between ambient and maximum.

The dough and set times and maximum exotherm temperatures are very important parameters that determine how the hardenable compositions are to be used. Compositions hardenable at room temperature (so-called "self-curing" or "cold-curing" systems) have dough times that are typically 4 to 10 minutes and set times that are typically 10 to 25 minutes in duration. These parameters effectively define the time period available for the operator to manipulate the dough in the desired fashion, for example pressing into a denture mould for denture base manufacture, or pressing into a bone cavity during hip repair or replacement or injecting into a vertebral cavity during spinal surgery or forcing into a gap or cavity during industrial cementing operations. There is an obvious desire to maximise the working time available to the operator. This should ideally be achieved without an increase in the set time as this defines the end point for the cementing or fixing operation. This therefore focuses attention on shortening the dough time. The dough time is determined by the rate at which the combination of solid and liquid components rises in viscosity immediately after mixing and is controlled by a number of factors, such as polymer bead particle size and shape, polymer molecular weight, and polymer composition.

U.S. Pat. No. 5,650,108 (Nies et al) describes use of a bead mill to treat a mixture of PMMA beads and granules. The resulting polymer mixture is then stirred with the liquid component to yield a composition that doughs after about 2 minutes.

US2007/0213425 A1 (Higham and He) teaches the use of a ball mill or jet mill to produce milled PMMA or PMMA copolymer beads that display shortened dough times compared to the un-milled beads after mixing with the liquid component of a bone cement.

U.S. Pat. No. 4,268,639 (Seidel et al) describes fast doughing self-curing compositions based on mixtures of PMMA and poly(2-hydroxyethyl methacrylate) (PHEMA) as the solid component and MMA and/or 2-hydroxyethyl methacrylate (HEMA) as liquid component. Dough times as short as 2 minutes and work times of at least 6 minutes are described.

US2007/0032567 A1 (Beyar et al) describes fast doughing bone cement compositions that reach a viscosity of at least 500 Pascal seconds within 180 seconds after mixing monomer and polymer components, and a working window of at least 5 minutes. The characteristics are said to be obtained through the use of beads of different size distributions. The beads less than 20 microns in diameter are said to facilitate rapid wetting with monomer liquid and contribute to a fast transition to a viscous state.

The influence of PMMA bead size on the rheological properties of bone cements has been studied by Hernandez, L.; Goni, I.; Gurruchaga, M., "Effect of size of pmma beads on setting parameters and rheological properties of injectable bone cements", Transactions—7th World Biomaterials Congress, Sydney, Australia, 17 May 2004-21 May 2004, p 740. The authors note that "With increasing the fraction of small beads . . . , the onset of the increasing viscosity appears sooner. This is due to the solvation of the smallest PMMA beads (<20 microns), which causes an increase of viscosity of the polymerizing mass". Also, "In conclusion, we can say that it is feasible to obtain injectable bone cements with optimal rheological properties by means of mixing beads of different sizes".

Another paper that describes how the rheological properties of acrylic bone cement are influenced by the PMMA bead particle size is: Lewis G. and Carroll M, J Biomed Mater Res (Appl Biomater) 63: 191-199, 2002. The authors conclude that one of the factors that strongly influence the rheological properties is the relative amount of small-sized PMMA beads (mean diameter between 0 and 40 microns).

A study on the doughing time of heat-cured dental resins (McCabe, J. F., Spence D. and Wilson H. J., Journal of Oral Rehabilitation, 1975 Volume 2, pages 199-207) concluded that " . . . the concept of short doughing time depends upon the presence of considerable numbers of small beads." The particle diameter of small beads is inferred as D<20 microns.

From the above description, it can be seen that the most commonly described methods of achieving short dough time are to subject the PMMA polymer particles to milling or to deliberately incorporate a significant proportion of PMMA polymer particles of <20 microns in diameter into the solid component of the hardenable composition. Milling processes suffer from the disadvantages of being limited in the amount of beads that can be milled at one time, leading to long manufacturing times if significant quantities of material are involved.

Additionally, the problems of batch to batch reproducibility, cleaning the mill between batches and introduction of contamination during the significant amount of processing and manual handling need to be overcome. Controlling the relative amount of <20 microns diameter PMMA polymer particles in the solid component is not straightforward. PMMA beads used in hardenable compositions are generally produced by a suspension or dispersion polymerization process. This involves polymerizing dispersed MMA monomer droplets in a liquid phase, usually water, to form solid spherical beads, which are then separated from the liquid phase by a filtration step, washed to remove dispersing agents, dried and then sieved. However, particles <20 microns diameter are relatively difficult to filter and wash, involving long and often laborious processing times.

An alternative means of collecting a significant proportion of small (<20 microns diameter) PMMA polymer particles is use of a sieving process to separate out the smallest particle size fraction from a conventionally prepared suspension polymerization slurry. However, the yields are relatively low, sieving times can be long and the problem remains of what to do with the rather large amount of coarser particle size material that is retained on the sieves.

Another approach to generating a significant proportion of small (<20 microns diameter) PMMA polymer particles is to use mechanical methods to break down the beads of a conventionally produced material, e.g., by milling, grinding, crushing, etc. However, PMMA beads are relatively hard and so long processing times are usually required to achieve significant increase in the proportion of small (<20 microns diameter) PMMA polymer particles (typically >24 hours for ball milling). Additionally, the batch to batch repeatability of such a process is quite poor, sometimes necessitating further processing of the resultant product, e.g., by sieving or blending, to achieve the desired particle size distribution.

This makes the commercial manufacture of PMMA with a significant proportion of particles <20 microns in diameter an expensive and sometimes tedious and unreliable undertaking.

WO 2010/018412 teaches a solution to the problem of how to achieve short dough time through the use of a network of coalesced emulsion polymerized acrylic microparticles as part of the solid polymer component. The network of coalesced emulsion polymerized microparticles forms a porous or microporous acrylic polymer particle. The polymer particles are formed by drying of the liquid emulsion to form a powder, with the preferred means of drying the emulsion polymer microparticles being spray drying. After drying the coalesced particle, it is used as the solid component of the hardenable two part acrylic composition.

WO98/24398 (Lautenschlager et al) describes a bone cement system of low porosity prepared by mixing together two liquid components. Each liquid component consists of solutions of PMMA in MMA monomer, with one solution containing an initiator (e.g., BPO) and the other solution containing an activator (e.g. DMPT). This system has the disadvantages of limited storage stability, a relatively high polymerization exotherm and an increased shrinkage that is produced by the necessarily higher levels of MMA required to prepare the solutions.

WO2010/005442 (Hasenwinkel et al) overcomes these disadvantages to some extent by incorporating cross-linked PMMA beads into the solutions. However, the disadvantage of limited storage stability remains.

US2011/0054392 and EP 2,139,530 (Nies) describes an implant material for improved release of active ingredients comprising two components. The first component comprises a mixture of polymer powder and BPO initiator that is made into a stable non-settling paste by adding water, surface active agent (e.g. Tween 80) and a water soluble polymer (e.g., carboxymethyl starch). The second component comprises a solution of PMMA dissolved in MMA monomer plus DMPT accelerator. Each component is charged to separate compartments of a double chamber syringe and mixed by pressing through a static mixer. The high water content provides high porosity in the final hardened product facilitating the improved release of active ingredients. However, the relatively high porosity (typically approximately 16% and higher) creates the disadvantage of reduced mechanical properties, e.g. a reduced compression strength that is less than acceptable for conventional bone cements.

Additional prior art documents De Wijn, J. Biomed. Mater. Res. Symposium, No 7, pp 625-635 (1976), U.S. Pat. No. 4,093,576, Boger et al., J. Biomed. Mat. Res. Part B: Applied Biomaterials, volume 86B, part 2, pp 474-482 (2008) and WO2004/071543 discuss the inclusion of water in a bone cement system, but not for the purpose of delivery via a double chamber syringe and mixing by pressing through a static mixer.

De Wijn in J. Biomed. Mater. Res. Symposium, No 7, pp 625-635 (1976) and in U.S. Pat. No. 4,093,576 describes mixing of a conventional polymer powder with a gelling agent in powder form, e.g. carboxymethylcellulose (CMC). Monomer is then added to form a cement dough, followed by the addition of water to produce gelling with the CMC. The resultant mixture is then cured to form a porous material. The open pore structure of the porous material is said to allow for tissue invasion over time to further anchor the implant with surrounding connective tissue or bone. However, the porous nature of the material again creates the disadvantage of reduced mechanical properties compared to conventional bone cements.

Boger et al in J. Biomed. Mat. Res. Part B: Applied Biomaterials, volume 86B, part 2, pp 474-482 (2008) and Bisig et al in WO2004/071543 describe an injectable low modulus PMMA bone cement for osteoporotic bone. This system consists of three components, namely the powder and liquid components of a conventional two-component bone cement, plus an aqueous solution of hyaluronic acid. Porous materials result that are claimed to have mechanical properties close to that of human cancellous bone, significantly lower than the mechanical properties of conventional bone cement.

A further problem can arise when mixing a liquid first part and a liquid second part such as through a static mixer connected to twin compartments of a syringe or caulking gun if the viscosity of one or both of the liquids is too high or the viscosity of the liquids are significantly different to each other.

One solution to the problem is to reduce the viscosity of the liquid first part and match it more closely to the viscosity of the liquid second part.

High viscosity of the liquid first part could be reduced simply by increasing the amount of liquid carrier (e.g. water) in the liquid first part. However, higher levels of water in the reacted two part acrylic composition increase the amount of porosity and therefore reduce the mechanical properties in the bone cement.

Surprisingly, methods have also been discovered that reduce the viscosity of the liquid first part without resorting to undesirable methods such as increasing the amount of water as liquid carrier.

One or more objects of the present invention is to provide a solution to one or more of the above problems.

According to a first aspect of the present invention there is provided a hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, wherein the said monomer component and the said initiator component are located in separate parts of the said two part composition so that the monomer component is storage stable characterized in that the liquid first part comprises emulsion polymerized acrylic polymer particles in a liquid carrier.

Preferably, the emulsion polymerized particles in a liquid carrier are in the form of an acrylic polymer emulsion. The liquid carrier is preferably water. Accordingly, the polymer emulsion is preferably an aqueous emulsion. The water carrier may include other components. These components may be dissolved in the water such as solubilizing agents selected from: —polyethylene glycol, glycerol and D-sorbitol.

The acrylic polymer emulsion may provide a continuous phase for the liquid first part. The acrylic polymer emulsion typically consists of emulsion polymerized acrylic polymer particles, at least one emulsifier and water.

In one alternative set of embodiments, the invention extends to a hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, characterized in that the liquid first part comprises emulsion polymerized acrylic polymer particles in a liquid carrier.

Typically, the liquid second part comprises the monomer component. This set of embodiments may also have any of the features of the first or further aspects herein unless such features are mutually exclusive.

Benefits

Advantageously, the composition includes an acrylic polymer emulsion which provides a liquid carrier for the emulsion polymerized acrylic particles, typically microparticles, suspended therein so that the normally solid polymer powder component of the composition is instead provided as a liquid. The liquid emulsion first part or the liquid second part may each also have independently suspended therein further components of the composition.

Additionally, through use of the emulsion polymerized acrylic particles directly as prepared in their primary emulsion form, the additional benefit is offered in some embodiments of being able to store and deliver each component of the hardenable composition as a liquid such as an emulsion, dispersion, paste or solution within separate compartments of a double chamber syringe or caulking gun. These components can then be conveniently mixed and delivered directly to the required site as required by pressing in tandem through a mixing tip applied to the syringe/caulking gun such as a static mixer or helical mixer applied to the syringe/caulking gun, thereby overcoming the inconvenience of manual mixing. In addition, the mixing of the hardenable composition is more reproducible, safer and reliable.

Furthermore, storing the individual components in respective chambers of a double chamber syringe or caulking gun provides the benefits of avoiding the risk encountered in manual mixing of exposure to hazardous monomers by operators. Mixing is achieved directly during applying of the cement to the desired site.

In addition, it is also possible in some embodiments to provide a disposable mixing tip so that the double chamber syringe or caulking gun may be used on more than one occasion by attaching a further mixing tip. Double chambers have not hitherto been possible because conventional powder cannot be pushed out into the nozzle. Therefore, it is necessary to mix the powder and liquid components prior to placement in a single chamber syringe. Such a mixture is not storage stable so the option of later re-using the barrel of material with a replacement mixing tip head was not possible.

A further advantage of the invention is that the components of the two part composition have long storage stability.

A further advantage to the invention is that the emulsion polymerized acrylic particles can be used directly in a liquid emulsion to produce a hardenable composition with shortened dough time without having to produce a network of coalesced emulsion polymerized microparticles formed by drying of the liquid emulsion to form a powder. This therefore saves significant energy costs and improves manufacturing efficiency.

The two part hardenable compositions of the invention also attain a low maximum exotherm temperature during hardening thus avoiding in the case of bone cements, tissue necrosis, a well known problem of acrylic bone cements.

The hardenable compositions formed from the invention also display a long working time thereby providing a longer time period for the operator to manipulate the cement dough in the desired fashion during application.

Advantageously, because of the presence of the water in the liquid first part, the final cured hardened cement composition is porous. This porosity allows the mechanical properties of the hardenable composition to be matched to those of e.g., vertebral bone, thereby avoiding well known problems associated through implantation of artificial materials that are higher in modulus than the surrounding natural bone. However, the formulation can be also altered to adjust the level of porosity and vary the mechanical properties, e.g., to achieve mechanical properties that satisfy the requirements of ISO 5833:2002.

In addition, as a result of the porosity, the polymerization shrinkage upon setting of compositions of the invention may be lower than would normally be expected of conventional hardenable compositions based on powder/liquid combinations.

A still further advantage of the invention when used as a bone cement is that the control of porosity (size and topography) allows improved control over the controlled release of antibiotics and other medicines into the surrounding bone and tissue.

Polymer Beads

As mentioned above, the liquid first part contains emulsion polymerized acrylic particles, preferably microparticles. Preferably, the two part acrylic composition also comprises at least one further type of acrylic polymer particles. Preferably, the at least one further type(s) of acrylic polymer particles are polymer beads. Such beads are preferably not formed of emulsion polymerized particles but are preferably produced by conventional polymer processing. Such polymer beads are well known to the skilled person in the field of acrylic polymer compositions and may, for example, be those made by bulk, solution or suspension polymerization. Typically, the beads are made by suspension polymerization. There may be more than one further type of acrylic polymer particles in the two part acrylic polymer composition which are differentiated from each other by average particle size and/or molecular weight. For instance there may be two, three or four such further types of acrylic polymer particles. Mixing of the beads with the liquid first part forms a dispersion of the polymer beads in the liquid carrier. Typically, this is a dispersion of the bead polymer in a continuous emulsion phase.

The term beads as used herein is not meant to be interpreted restrictively unless indicated otherwise and refers to a discrete polymer particle of any suitable size, shape and surface texture.

Polymer and Other Component Amounts

Typically, the polymerized emulsion particles and, if present, further types of polymer particles form at least 98% of the polymer present in the two part acrylic composition prior to mixing, more preferably, at least 99%, most preferably, approximately 100% of the polymer present in the two part acrylic composition prior to mixing. Upon mixing the monomer polymerizes and causes the mixed composition to form a cement which gradually hardens eventually setting to a solid.

Typically, the solids content of the liquid first part of the two part composition is in the range 10-95% w/w, more typically, 20-92% w/w, most typically, 30-90% w/w. The preferred ranges depend on the properties that are desired, e.g. mechanical properties. For example, to achieve a compressive strength in the resulting solid of greater than 40 MPa, the preferred range of solids content of the liquid first part of the two part composition is 60-95% w/w, more preferably, 65-95% w/w, most preferably, 70-90% w/w.

The total of emulsion polymerized acrylic polymer particles and, if present, further types of polymer particles typically form between 50-99.9% w/w of the solids content of the first part of the two-part acrylic composition, more preferably, 60-97.5% w/w, most preferably, 65-94.5% w/w. The balance is generally made up of other solids which may be fillers, pigments, dyestuffs, catalysts, and initiator, although residual emulsifier may also be present.

The ratio of the emulsion polymerised acrylic polymer particles of the aspects of the invention to the total said further type of acrylic polymer particles, if present, varies depending on the final application. Nevertheless, it is advantageous in some applications such as bone cements to have a ratio thereof of between 2:98 to 50:50 w/w thereof, more preferably, 3:97 to 40:60 w/w, most preferably, 5:95 to 30:70 w/w. Such a ratio gives a good balance between short dough times and long work times. However, no restriction should be taken hereby and other higher emulsion polymerized particle ratios are also possible such as 100% w/w emulsion polymerized particles forming the polymer component of the first part or a ratio of 30:70 to 70:30, more typically, 40:60 to 60:40.

The liquid carrier of the first part is sufficient to act as a liquid carrier for the solid components whether emulsified or otherwise suspended therein. The liquid may thus form between 5-90% w/w of the liquid first part, more typically, 8-80% w/w, most typically, 10-70% w/w.

The liquid second part may include monomer, water or other solvent as the liquid component which is sufficient to provide a liquid carrier for the other components which may include other polymer composition components known to the skilled person such as polymer, initiator (if monomer is absent), fillers, pigments, dyestuffs, catalysts, accelerators, plasticisers etc. In this regard, although it is possible to use an initiator paste in a liquid carrier such as water or organic solvent, optionally in the presence of plasticizer to form the liquid second part, it is more typical to have acrylic monomer as the liquid carrier in the second part, optionally with acrylic polymer particles dissolved therein and with other components added such as accelerators, fillers, dyes etc. Generally, the amount of monomer in the unmixed composition, whether in the second part, or first part, is in the range 10-70% w/w, more typically 15-60% w/w, more preferably 20-50% w/w.

When both monomer and the further type of acrylic polymer particles form the bulk of the liquid second part, the ratio of acrylic monomer:polymer is in the range 99:1 to 60:40 w/w.

The ratio of the liquid first part to the liquid second part is preferably in the range 2:1 to 1:20 by mass, more preferably, 1:1 to 1:2 by mass.

Typically, the level of filler in the two part acrylic composition is 0-49.9% w/w of the acrylic composition, more preferably, 2-39.9% w/w, most preferably, 5-34.9% w/w. The filler may be present in either one of the two parts or may be distributed in both parts.

Accelerators may be present in the unmixed composition in the range 0.1 to 5% by mass, more typically, 0.5-3% by mass.

The total level of unreacted initiator, whether residual or added, in the two part acrylic composition is typically, 0.1-10% w/w of the acrylic composition, preferably, 0.15-5% w/w, more preferably, 0.2-4.0% w/w.

Where initiator is used in one of the components, this may be encapsulated within the polymer bead or polymer emulsion or separately added.

Where polymer is dissolved in monomer, the polymer must contain very low levels of residual initiator to avoid shortening of the shelf life.

The initiator may be present in both the first and, if present, further types of polymer particles that form the acrylic polymer composition. The initiator in the first and, if present, further polymer particles may be the residual amount of unreacted initiator used in the formation of the particles which is therefore the equivalent of the excess amount of initiator. Some initiator can alternatively or additionally be added as a separate component to the two part composition. In the emulsion polymerized acrylic particles, the level of residual initiator present before reaction with the second part is typically, 0.001-10% w/w of the emulsion polymerized acrylic particles, preferably, 0.1-6% w/w, more preferably 0.1-5% w/w.

Preferably, the initiator is present at a level which will effect polymerization of the monomer component that is at least greater than 90% polymerization, more typically, greater than 93%, more typically greater than 95% polymerization.

The liquid component of the liquid first part may be water or other liquid such as monomer, organic solvent, plasticizer, liquid polymer, diluent, more typically, water and optionally acrylic monomer.

If more than one type of acrylic polymer particle is present in the first part, the additional types of polymer particles are either mixed with the first part emulsion to form a suspension in the water emulsion phase or dissolved in monomer (in the case of the initiator being in the $2^{nd}$ part) to form a solution which is suspended in the continuous emulsion phase, or alternatively the emulsion is suspended in a continuous monomer solution phase. In any case, the polymer components are typically, in the presence of suitable other polymer composition components known to the skilled person. Such polymer composition additives include initiators, emulsifiers, catalysts, pigments, dyestuffs and fillers.

Specific Materials

Initiators that can be used to initiate the emulsion polymerization and therefore those which may form residual initiators in the composition to initiate the hardening process are persulphates, (e.g., potassium, sodium or ammonium), peroxides (e.g., hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

In addition to the emulsion initiators above, a particularly preferred initiator for the hardening stage is dibenzoyl peroxide.

Initiators that can be used for emulsifier free emulsion polymerization and therefore which may be present as residual initiators include: —ionic water-soluble initiators, such as potassium, sodium or ammonium persulphate.

In addition, any one or more of the above initiators can be added to the composition independently.

In a particularly preferred embodiment, the emulsion particles incorporate the initiator in their polymer matrix. Accordingly, in this embodiment, the initiator is not added separately to the liquid first part of the composition.

Advantageously, the initiator for the hardenable composition can be added as excess initiator during the emulsion polymerization of the particles so that some initiator is used in the polymerization of the emulsion particles but as the emulsion particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerization process and, accordingly, excess initiator is used in the final shell polymerization stage. During polymerization of the first or further type of polymer particle more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

For the avoidance of doubt, by "excess initiator" is meant, the portion of initiator that is not required to complete polymerisation of the acrylic polymer particles and is available for subsequent reaction after the initial polymerization of the acrylic polymer particles is terminated.

Preferably, the emulsion polymerized acrylic particles of the liquid composition incorporate a suitable initiator compound in their polymer matrix, in the case of multistage emulsion particles, the initiator is incorporated in their outer shell in the final stage.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT) in the acrylic monomer composition can also affect the set time. Increased accelerator concentration results in shortened set time.

In medical and some dental applications, the filler is advantageously an x-ray opaque filler so that it can be observed during treatment or surgery by x-ray. Suitable fillers for this purpose include barium sulphate and zirconium dioxide, either encapsulated within the polymer particles or free. In the production of dentures or in industrial applications, other fillers may instead be used and these will be known to the skilled person in the art of such fields. Additionally, organic x-ray opaque monomers can be used instead of fillers. These can be copolymerized into any of the acrylic polymer particles during their production or incorporated into the acrylic monomer composition. Typical organic x-ray opaque monomers include halogenated methacrylates or acrylates, e.g., 2,3-dibromopropyl methacrylate or 2-methacryloyloxyethyl-2,3,5-triiodobenzoate.

Emulsifiers that can be used in the emulsion polymerization and therefore those which are present in the subsequent liquid first part are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxy ethyl)-N-octadecyl sulfosuccinate, sodium salt of sulphated alkylphenol ethoxylates, sodium alkane sulfonate, sodium dodecyl sulphate or sodium 2-ethylhexyl sulphate), nonionic (e.g., polyethylene glycol nonylphenyl ethers, polyethylene oxide octylphenyl ethers, or di-functional ethylene oxide/propylene oxide block copolymers) or cationic emulsifiers (e.g., hexadecyltrimethylammonium bromide or alkyl polyglycoletherammonium methyl chloride). Reactive or polymerisable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethylhexadecyldimethylammonium bromide.

The mixing of the further components of the liquid first part with the liquid carrier may be carried out by any suitable technique known to the skilled person for mixing solids or liquids with a liquid.

Preferably, the Z-average particle size of the emulsion polymerized acrylic polymer particles is less than 2000 nm as determined by light scattering using a Malvern Zetasizer nano series S particle size analyzer (adding one drop of emulsion to 1 ml of de-ionised water in a measurement cuvette, allowing the test sample to equilibrate at 25° C. and determining Z-average particle size using the software provided by the instrument), more preferably, less than 1000 nm, most preferably, less than 800 nm, especially, less than 500 nm. A preferred Z-average particle size range for the emulsion polymerized particles is between 10-2000 nm, more preferably, 20-1000 nm, most preferably, 50-500 nm, especially 100-450 nm, as determined by light scattering using a Malvern Zetasizer as above.

The core shell (C:S) ratio of the emulsion polymerised acrylic particles is typically, between C:S 95:5% wt and C:S 40:60% wt, more typically, between C:S 90:10% wt and C:S 50:50% wt, preferably, between C:S 85:15% wt and C:S 70:30% wt.

Typically, the emulsion polymerized acrylic polymer particles may be single stage or multistage i.e. the so called core/shell particles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion particles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulphate) or through using emulsifiers. Once the seed particles are formed, the core and shell are formed from sequential addition of further aliquots of monomer and initiator.

The Brookfield viscosity range for the liquid first part and liquid second part may be between 10 and 10,000 centipoise, more preferably between 500 and 7,000 centipoise, still more preferably between 1,000 and 5,000 centipoise, most preferably between 1,500 and 4,000 centipoise.

A particular problem in the case where the liquid first part is comprised of a mixture of emulsion polymerized acrylic polymer particles and a further type of acrylic polymer particle, e.g. an acrylic polymer bead is that the viscosity of the liquid first part can be relatively high in comparison to the liquid second part, particularly when the liquid second part is a relatively low viscosity syrup composed of an acrylic polymer dissolved in acrylic monomer. As mentioned above, it can be problematic if the viscosity of one or both of the liquids is too high or the viscosity of the two or more liquids are significantly different to each other.

In the present invention, it is therefore advantageous to control the viscosity of the liquid first part so that the viscosity is lowered to a level that provides a suitable viscosity for delivery of the two part bone cement from separate respective containers of a device having two or more containers, such as a twin barrelled syringe, to the outlet thereof. Typically, such devices also require a mixer to mix the extrudate of the multiple containers together before the outlet, such as a static mixer. The increasing viscosity of the hardening composition as it travels through the mixer towards the outlet of the device can be influenced by the viscosity of the liquid first part. Controlling the viscosity of the liquid first part may be achieved by adapting the components of the first part by:

(i) providing emulsion polymerized acrylic polymer particles of the invention first part with a relatively large z-average particle size; and/or
(ii) providing a second or further population of emulsion polymerised acrylic polymer particles in the first part having different respective z-average particle sizes from the first emulsion polymerised acrylic polymer particles of the invention; and/or
(iii) providing two or more further types of acrylic polymer particle populations in the first part said further types having different respective mean diameter particle sizes from each other.

Accordingly, the z-average particle size of the emulsion polymerized acrylic polymer particles and/or the second or further populations of emulsion polymerised acrylic polymer particles may independently be greater than 100 nm, more preferably greater than 200 nm, for instance, in the range 100-900 nm, most preferably 200-800 nm.

Furthermore, the mean diameter particle size of the further acrylic polymer particles may be 10-1,000 microns, preferably 15-600 microns, more preferably 20-400 microns, most preferably 25-300 microns.

Therefore, according to a second aspect of the present invention there is provided a hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, characterized in that the liquid first part comprises in a liquid carrier a first population of emulsion polymerized acrylic polymer particles and a second or further population/s of emulsion polymerised acrylic polymer particles having different z-average particle size/s from the first emulsion polymerised acrylic polymer particles.

Preferably, the said monomer component and the said initiator component are located in separate parts of the said two part composition so that the monomer component is storage stable.

Therefore, according to a third aspect of the present invention there is provided a hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, characterized in that the liquid first part comprises in a liquid carrier a first population of emulsion polymerized acrylic polymer particles and two or more further types of acrylic polymer particle populations said further types having different respective mean diameter particle sizes from each other.

Preferably, the said monomer component and the said initiator component are located in separate parts of the said two part composition so that the monomer component is storage stable.

Preferably, where there are two or more population/s of emulsion polymerised acrylic polymer particles there is at least 1 wt % of each type, more preferably, 5 wt %, most preferably, 10 wt %. For example, where there are two types the typical ratios are in the range 1-99:99-1 wt %, more typically, 10-90:90-10 wt %. For further example, where there are three types, the typical ratios are in the range 1-98:98-1:98-1 wt %, more typically, 5-90:90-5:90-5 wt %.

Preferably, where there are two or more population/s of further types of acrylic polymer particles there is at least 1 wt % of each type, more preferably, 5 wt %, most preferably, 10 wt %. For example, where there are two types the typical ratios are in the range 1-99:99-1 wt %, more typically, 10-90:90-10 wt %. For further example, where there are three types, the typical ratios are in the range 1-98:98-1:98-1 wt %, more typically, 5-90:90-5:90-5 wt %.

Preferably, the compressive strength of the solid produced by mixing the said first and second part in any aspect of the present invention is greater than 40 MPa, more preferably greater than 70 MPa. The typical range of compressive strengths found in the produced solid is 40-130 MPa, more preferably 70-130 MPa.

Definitions

By "located in separate parts" is meant that if the said monomer component is located in the first part then the said initiator component is located in the second part and vice versa.

The term "liquid" herein does not require definition because it is well understood by the skilled person. However, for the avoidance of doubt it includes a flowable material such as a slurry or paste that is thus susceptible of delivery through a syringe or caulking gun outlet by the application of pressure. Typically, the term liquid applies at least between 5 and 35° C., more typically, between 5 and 30° C.

By "storage stable" is meant that the monomer or liquid does not polymerize under normally acceptable storage conditions of temperature and time i.e. between 5 and 30° C. and 1 to 250 days, more typically, 15 to 25° C. and 1 to 170 days.

The term "population" is generally understood by the skilled person but for the avoidance of doubt refers to a plurality of polymer particles having a specific mean particle size, weight average molecular weight, particle size distribution and molecular weight distribution as is usually produced by monomer(s) which have undergone the same polymerization process(es) together.

As mentioned above, the polymer composition of the invention may include further types of acrylic polymer particles.

The method of manufacture of such further particles is generally conventional suspension or dispersion polymerization to produce generally spherical polymer particles, or beads. However, other methods of manufacture are also possible, e.g., bulk polymerization or solution polymerization followed by evaporation of the solvent.

By acrylic polymer herein whether in relation to the emulsion polymerised acrylic polymer particles or the at least one further type of acrylic polymer particles is meant independently for each type a homopolymer of a polyalkyl (alk)acrylate or (alk)acrylic acid or copolymers of a alkyl (alk)acrylate or (alk)acrylic acid with one or more other vinyl monomers. Typically, a homopolymer of methyl methacrylate or a copolymer of methyl methacrylate with one or more other vinyl monomers is used. By other vinyl monomers is meant a further alkyl(alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid, acrylic acid; hydroxyl-functional acrylates such as 2-hydroxyethyl methacrylate, hydroxypropylethyl methacrylate,2-hydroxyethyl acrylate, or hydroxypropyl acrylate; vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers.

Copolymers containing functionalized monomers are of special interest because they may help in dispersing the X-ray radio-opacifying fillers used in bone cement compositions (e.g. barium sulphate, zirconium dioxide, etc) into the liquid second part. Suitable functionalized monomers are well known in the field of pigment dispersion in inks and coatings. For example, amines such as N,N-dimethylaminoethyl methacrylate, N,N-diethylaminoethyl methacrylate, t-butylaminoethyl methacrylate and acids such as methacrylic acid and acrylic acid.

Crosslinking monomers can be used to crosslink one of the acrylic polymer particle types. For the emulsion polymerized particles, crosslinking may be carried out in the core and the shell, or only the core, or only the shell. Crosslinking serves the purpose of fine tuning the properties of the hardenable two part acrylic composition.

The weight average molecular weight (Mw) of the emulsion polymerized acrylic polymer particles is typically, between 25,000 daltons and 3,000,000 daltons, more typically, between 100,000 daltons and 1,500,000 daltons, preferably, between 250,000 and 1000000, for instance, between 250,000 and 600,000. Molecular weight may be determined for this purpose by gel permeation chromatography (GPC).

Although, the molecular weights of the polymers in the polymer components of the hardenable composition may influence the dough and work times, the invention is not restricted to any particular molecular weight. In any case, reductions in the molecular weight and/or increases in the particle size of the further acrylic polymer particles can be used to increase the work time of the hardenable composition.

The weight average molecular weight (Mw) of the further type of polymer particles, if present, is typically, between 10,000 daltons and 3,000,000 daltons, more typically, between 30,000 daltons and 1,000,000 daltons, preferably, between 50,000 and 700,000, for instance, between 60,000 and 600,000 Daltons. Molecular weight may be determined for this purpose by gel permeation chromatography (GPC).

By acrylic monomer herein is meant any suitable alkyl (alk)acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers. Typically, methyl methacrylate is used.

The acrylic monomer of the invention is optionally, provided with an accompanying suitable inhibitor such as hydroquinone (HQ), methyl hydroquinone (MeHQ), 2,6-di-tertiary-butyl-4-methoxyphenol (Topanol O) and 2,4-dimethyl-6-tertiary-butyl phenol (Topanol A). The inhibitor is present to prevent the monomer from spontaneously polymerising. A suitable inhibitor is 60 ppm of hydroquinone to ensure long shelf life at room temperature.

Polymerization activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for industrial applications the use of heat in "heat-cure" systems is also possible. For instance, dentures can be activated by heat.

By alkyl herein is meant $C_1$-$C_{18}$ alkyl wherein the term alkyl and alk encompasses cyclooalkyl and hydroxyl functional $C_1$-$C_{18}$ alkyl. By alk herein is meant $C_0$-$C_8$ alk.

In one preferred embodiment, the acrylic polymer composition liquid first part comprises the emulsion of polymerized acrylic polymer particles and only a single type of further acrylic polymer particle, the former generally to control the dough time and the latter to generally control the working time.

By "acrylic composition" is meant a composition where at least 50% of the total monomer and monomer residues present are present as or derived from one or more of the above defined acrylic monomers, more typically, is meant at least 70%, most typically, 95% or especially, 99% of the total.

In a preferred embodiment of the invention the first part comprises emulsion polymerized acrylic polymer particles in a liquid carrier (preferably, PMMA emulsion) and initiator and the second part comprises acrylic monomer (preferably MMA monomer) and accelerator.

In a further preferred embodiment of the invention the first part comprises emulsion polymerized acrylic polymer particles in a liquid carrier (preferably PMMA emulsion) and initiator and the second part comprises a solution of initiator-free acrylic polymer (preferably PMMA), in acrylic monomer (preferably MMA) with accelerator.

In a further preferred embodiment of the invention the first part comprises acrylic polymer bead (preferably PMMA bead) and emulsion polymerized acrylic polymer particles in a liquid carrier, (preferably, PMMA emulsion) and initiator and the second part comprises acrylic monomer (preferably, MMA monomer) and accelerator.

In a further preferred embodiment of the invention the first part comprises acrylic polymer bead (preferably PMMA bead) and emulsion polymerized acrylic polymer particles in a liquid carrier, (preferably, PMMA emulsion) and initiator and the second part comprises a solution of initiator-free acrylic polymer bead (preferably PMMA bead) in acrylic monomer (preferably, MMA monomer) and accelerator.

In a further preferred embodiment of the invention the first part comprises a solution of initiator-free acrylic polymer bead (preferably PMMA bead) in acrylic monomer (preferably, MMA monomer) and initiator-free emulsion polymerized acrylic polymer particles in a liquid carrier, (preferably, PMMA emulsion) and the second part comprises initiator paste. Initiator pastes are available commercially usually as a mixture with water or plasticiser.

According to a further aspect of the present invention there is provided a method of producing a hardenable two part acrylic composition comprising a storage stable liquid first part and a storage stable liquid second part which react with each other upon mixing to form a cement which hardens to a solid, comprising the steps of: —
(a) emulsion polymerizing at least one acrylic monomer composition in the presence of excess initiator to produce an acrylic polymer emulsion with residual initiator; or
(b) emulsion polymerizing at least one acrylic monomer composition to produce an acrylic polymer emulsion and optionally adding initiator to the emulsion;
(c) optionally, mixing the emulsion from (a) or (b) with at least one further type of acrylic polymer particles and/or a solution of the said further type of acrylic polymer in acrylic monomer, to produce a liquid acrylic polymer first part suitable for hardening at a predetermined rate in the joint presence of an acrylic monomer composition and initiator;
(d) contacting the acrylic polymer first part with either acrylic monomer or initiator so that the said first part is in joint contact with an initiator and an acrylic monomer to thereby form a cement that will harden.

More specifically, in accordance with a still further aspect of the present invention there is provided a method of producing a hardenable two part acrylic composition comprising a storage stable liquid first part and a storage stable liquid second part which react with each other upon mixing to form a cement which hardens to a solid, comprising the steps of: —
(a) emulsion polymerizing at least one acrylic monomer composition in the presence of excess initiator to produce an acrylic polymer emulsion with residual initiator; or
(b) emulsion polymerizing at least one acrylic monomer composition to produce an acrylic polymer emulsion and adding initiator to the emulsion; or
(c) emulsion polymerizing at least one acrylic monomer composition to produce an acrylic polymer emulsion without excess initiator;
(d) optionally, mixing the emulsion from (a) or (b) with at least one further type of acrylic polymer particles or mixing the emulsion from (c) with a solution of the said further type of acrylic polymer in acrylic monomer, to thereby produce a liquid acrylic polymer first part suitable for hardening at a predetermined rate in the joint presence of an acrylic monomer and initiator. Advantageously, in the present invention the monomer and initiator are kept in separate parts of the two part composition so that monomer is added from the 2nd part when unreacted initiator is present in the first part and so that initiator is added from the 2nd part when no unreacted initiator but instead monomer is present in the first part.

Preferably, step (a) comprises seed, core and at least one shell emulsion polymerization step. A particularly preferred method introduces an excess of initiator into the emulsion polymerization step (a) so that residual initiator is encapsulated within the emulsion particles. Preferably, in a multistage emulsion polymerization, the excess initiator is introduced during the final stage so that it is present in the outer shell of the multistage particle. However, alternatively, initiator can also be added subsequently to the acrylic polymer emulsion.

An advantage of the emulsion polymerized acrylic polymer particles of the first, second or third aspect of the invention is the rapid dough time that is reached in the presence of the acrylic monomer composition. However, the working time and set time for the dough need to vary depending on the application. If a very short working time and set time are required then the emulsion polymerized acrylic polymer particles of the first, second or third aspect of the invention may be used alone. Nevertheless, in most applications, a longer working time and set time will be required and this can be achieved by varying the amount, type and particle size of the further type of acrylic polymer particle. Polymer particles of smaller average particle size (e.g. typically <20 microns) are known to also give short working times but by increasing the amount of particles of larger particle size and by increasing the particle size itself, longer working times can be achieved. Accordingly, the particle size and amount of further acrylic polymer particles depends upon the final application and this will be appreciated by the skilled person.

Typically, the further type of acrylic polymer particle is in the form of a solid polymer particle known as a polymer bead. Such beads, as mentioned above, are typically produced by suspension polymerization although solution and bulk polymerization are also possible methods of production. Such beads may also contain encapsulated residual initiator as described for the emulsion polymerized acrylic polymer particles above. Although the average particle size of such beads is variable as mentioned above, depending upon the final application, a typical average particle size for such beads is in the range 10-1000 microns, more typically, 20-600 microns, most typically, 25-200 microns. The larger the average particle size, the longer the working time. The skilled person will also appreciate that the molecular weight of the polymer and the presence of accelerators can also influence the working time and the set time. An advantageous aspect of the present invention is therefore the reduced dough time achievable by the presence of the emulsion polymerized first type of acrylic polymer particles whereas the invention is not restricted to a particular working time or set time because this will depend on the application.

Notwithstanding the foregoing, a particularly advantageous application of the acrylic composition of the aspects of the invention is its use as bone cement compositions. Such compositions are used in vertebroplasty and demand very short dough times so that the operation may proceed without undue delay. In addition, such uses demand short set times so that immobilization of the patient in the operating site is not unnecessarily prolonged. A competing requirement is sufficient working time to carry out the procedure effectively. Shortening the dough time has the effect of increasing the work time. A similar application for the compositions of the present invention is dental repairs where similar short doughing times are required.

Nevertheless, short dough times can be seen as generally desirable in many industrial applications and therefore, the invention is not restricted to bone cement and dental applications although these are preferred embodiments.

Accordingly, the invention extends to the use of a liquid first part as defined in the first, second or third aspect of the invention as a dough time reduction agent in a hardenable two part acrylic composition.

Emulsion polymerized particles are well known in the field of impact modifiers. For this reason an impact modifier such as butadiene or butyl acrylate is typically introduced as a comonomer into one of the shells of the multistage core shell particle. However, in the two part compositions of the present invention, an impact modifier may not be required. Accordingly, the emulsion polymerized acrylic polymer particles of the present invention may be free from impact modifier co-monomer residues.

The acrylic composition first part of the present invention may be provided separately as a liquid either with or without added further components as defined herein for later use as a liquid first part in a hardenable composition.

Accordingly, according to a fourth aspect of the present invention there is provided a liquid composition comprising emulsion polymerized acrylic polymer particles, optionally, mixed with at least one further type of non-emulsion polymerized acrylic polymer particles, and optionally mixed with at least one further population of emulsion polymerized acrylic polymer particles and characterized in that there is a polymerization initiator in the liquid composition at a level sufficient to cause the liquid composition to harden upon contact with a reactive monomer liquid.

There is no particular temperature limitation on the use of the present invention. Generally, however, it is used at temperatures acceptable to the operator i.e. temperatures found during normal working conditions that may be encountered indoors or outdoors by the operator, for instance ambient temperature.

According to a further aspect of the present invention there is provided a solid cement composition produced from mixing a two part acrylic composition according to the first, second or third aspect of the present invention.

According to a further aspect of the present invention there is provided a process of producing an acrylic cement from a two part acrylic composition according to the first, second or third aspect of the present invention by mixing the said first and second parts.

The above process may be a manual mixing process. However, use of an adapted syringe or caulking gun is preferred.

Therefore, according to a further aspect of the present invention there is provided a syringe or caulking gun having at least two barrels comprising the liquid first part according to the first, second, third or fourth aspect of the present invention in a first barrel thereof and a liquid second part according to any aspect of the present invention in the second barrel thereof and also comprising the further components of the first, second, third or fourth aspect as disclosed herein.

The invention extends to a two part bone cement or dental cement or building cement or structural adhesive or laminating adhesive or jointing or sealing composition according to the first, second or third aspect of the present invention.

Preferably, in a bone cement or dental cement composition the components thereof are biocompatible components at least once the composition is set to a solid.

According to a still further aspect of the present invention there is provided a two part composition according to the first, second or third aspect of the present invention for use in the treatment of human or animal bone.

According to a still further aspect of the present invention there is provided a two part composition according to the first, second or third aspect of the present invention for use in the replacement of human or animal bone.

According to a still further aspect of the present invention there is provided a two part composition according to the first, second or third aspect of the present invention for use in the treatment of human teeth or animal teeth, hoof, nail or horn.

According to a still further aspect of the present invention there is provided a two part composition according to the first, second or third aspect of the present invention for use in the replacement of human teeth or animal teeth, hoof, nail or horn.

Embodiments of the invention will now be described with reference to the accompanying examples:—

EXAMPLES

Characterisation Techniques

The Z average emulsion particle size was determined using a Malvern Zetasizer nano series S particle size analyzer.

Reduced viscosity (RV, dl/g) was measured in chloroform (1 wt % solution) using an Ubbelohde viscometer type OB at 25° C.

Wt % residual dibenzoyl peroxide content was determined by a titration method.

Brookfield viscometry (BV, centipoise (cPs)) was carried out using a Brookfield Viscometer model RVDV-E at 25° C. operating with spindle number 5 and speed 20 rpm, except for examples 47 onwards for which the spindle and speed were adjusted depending on the viscosity range being measured Weight average molecular weight, Mw, was determined by gel permeation chromatography using polymethyl methacrylate standards for calibration. Tetrahydrofuran was used as the mobile phase.

Acrylic bead polymer mean diameter particle size was measured by a Coulter LS230 laser diffraction particle sizer.

Dough and set times and maximum exotherm temperature were measured according to BS ISO 5833:2002

The dough time is considered to be the length of time following the start of mixing for the mixture to achieve a dough-like mass that does not adhere to a gloved finger when gently touched.

The set time is considered to be the time taken to reach a temperature midway between ambient and maximum.

Flexural strength and flexural modulus were determined by a three-point bend test according to ISO 1567:1997. Compressive strength was determined according to ISO 5833:2002.

Examples 1 to 4 describe the preparation of acrylic emulsions of solids contents varying from 32% wt to 54% wt.

Example 1

Preparation of 32% wt Solids Acrylic Polymer Emulsion 2000 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 1000 grams methyl methacrylate, 1.8 grams of 1-dodecanethiol, 5.0 grams of sodium lauryl sulphate and 100 grams of deionised water. This mixture is stirred for 60 minutes prior to and throughout addition to keep it emulsified.

With the temperature of the water at 80° C., a polymer seed (Stage 1) is prepared by adding 100 grams of the emulsified monomer mixture to the flask followed by 10 milliliters of a 2 wt % solution of potassium persulphate in deionised water. Following a slight exotherm, the reaction proceeds for thirty minutes until the temperature returns to 80° C.

The core is then grown over the polymer seed particles (Stage 2) by firstly adding 10 milliliters of a 2 wt % solution of potassium persulphate in deionised water to the flask followed by continuous addition of 250 grams of the emulsified monomer mixture over approximately 45 minutes using a peristaltic pump. The reaction proceeds for a further 30 minutes after the completion of addition of the monomer mixture until the temperature returns to 80° C. This step is then repeated twice.

37.0 grams of 75% active dibenzoyl peroxide (BPO) are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 30 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The acrylic polymer emulsion has a solids content of 32% wt, reduced viscosity of 1.8 dl/g, residual dibenzoyl peroxide of 1.66% wt and a z-average emulsion particle size of 177 nm.

Example 2

Preparation of 38% wt Solids Acrylic Polymer Emulsion 1200 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 1000 grams methyl methacrylate (MMA), 1.0 grams of 1-dodecanethiol, 5.0 grams of sodium lauryl sulphate and 200 grams of deionised water. This mixture is stirred for 60 minutes prior to and throughout addition to keep it emulsified.

With the temperature of the water at 80° C., a polymer seed (Stage 1) is prepared by adding 100 grams of the emulsified monomer mixture to the flask followed by 10 milliliters of a 2 wt % solution of potassium persulphate in deionised water. Following a slight exotherm, the reaction proceeds for thirty minutes until the temperature returns to 80° C. To the remaining emulsified monomer mixture is added 1 g of sodium lauryl sulphate with stirring.

The core is then grown over the polymer seed particles (Stage 2) by firstly adding 10 milliliters of a 2 wt % solution of potassium persulphate in deionised water to the flask followed by continuous addition of 250 grams of the emulsified monomer mixture over approximately 45 minutes using a peristatic pump. The reaction proceeds for a further 30 minutes after the completion of addition of the monomer mixture until the temperature returns to 80° C. This step is then repeated twice.

35.0 grams of 75% active dibenzoyl peroxide are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 30 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The acrylic polymer emulsion has a solids content of 38% wt, reduced viscosity of 2.1 dl/g, Brookfield Viscosity of 50 cPs, residual dibenzoyl peroxide of 1.98% wt and a z-average emulsion particle size of 186 nm.

Example 3

Preparation of 50% wt Solids Acrylic Polymer Emulsion

The procedure of example 2 was repeated except 600 grams of deionised water are added to a five-liter round bottomed flask instead of 1200 grams.

The resultant acrylic polymer emulsion has a solids content of 50% wt, reduced viscosity of 1.6 dl/g, Brookfield Viscosity of 540 cPs, residual dibenzoyl peroxide of 2.10% wt and a z-average emulsion particle size of 205 nm.

Example 4

Preparation of 54% wt Solids Acrylic Polymer Emulsion

The procedure of example 2 was repeated except 400 grams of deionised water are added to a five-liter round bottomed flask instead of 1200 grams.

The resultant acrylic polymer emulsion has a solids content of 55% wt, reduced viscosity of 1.49 dl/g, Brookfield Viscosity of 7920 cPs, residual dibenzoyl peroxide of 2.20% wt and a z-average emulsion particle size of 191 nm.

Examples 5, 7 to 12 and 19 describe the preparation of the liquid first part by mixing the acrylic polymer emulsions prepared in examples 2 to 4 with acrylic bead polymers. Hardenable compositions are subsequently prepared by mixing the liquid first part with the liquid second part.

Example 5

Preparation of Liquid First Part Using 38% wt Solids Acrylic Polymer Emulsion

To a 250 ml polypropylene beaker equipped with electric stirrer motor and stainless steel paddle stirrer is added 70 g of poly(methyl methacrylate) (PMMA) bead polymer (Colacryl® B866, obtained from Lucite International Speciality Polymers & Resins Limited with RV of 2.4 dl/g, Mw 421,200, residual dibenzoyl peroxide 2.94% wt, mean particle size 39 microns). Stirring is commenced at 100 rpm and 30 g of the 38% wt solids acrylic polymer emulsion from example 2 is added over 60 to 90 seconds. The stirrer speed is then increased to 800-1000 rpm and mixing is continued for a further 3 to 5 minutes until a uniform liquid mixture is obtained. The Brookfield viscosity of the liquid mixture is 7,000 cPs. The liquid mixture is stable with no separation after storage at 23° C. for several days.

Example 6

Preparation of a Hardenable Composition

A hardenable composition is prepared by mixing 17.2 g of the liquid first part of example 5 with 7 ml of MMA monomer containing 60 ppm hydroquinone (HQ) inhibitor and 1% N,N-dimethyl-para-toluidine (DMPT) accelerator (liquid second part). The mix ratio used is 14 g polymer (equivalent dry weight) to 7 ml monomer liquid. Before mixing, the two components are equilibrated for at least 10 hours in an incubator at 23° C. The required amount of liquid first part is placed into a polypropylene beaker, followed by the liquid second part. Timing is started from the point of adding the liquid second part to the liquid first part. Hand mixing is then carried out for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass.

The following comparative examples were prepared to show the benefits of the invention over the prior art.

Comparative Example 1

The PMMA bead polymer stated in example 5 (Colacryl® 8866) is employed on its own with no acrylic polymer emulsion added. 14 g of this PMMA bead polymer is mixed with 7 ml of MMA monomer containing 60 ppm hydroquinone (HQ) inhibitor and 1% N,N-dimethyl-para-toluidine (DMPT) accelerator and tested as described above.

Comparative Example 2

This example is equivalent to example 6, except the acrylic polymer emulsion of example 2 is spray dried to form a powder before use. The blend ratio of PMMA bead polymer (Colacryl® B866) to the spray dried 38% wt solids emulsion of example 2 is 86/14% wt. 14 g of this blend of bead polymer and microporous acrylic polymer powder is then mixed with 7 ml of MMA monomer containing 60 ppm hydroquinone (HQ) inhibitor and 1% N,N-dimethyl-para-toluidine (DMPT) accelerator and tested as described above.

Table 1 records the results. It can be seen that example 6 displays a lower exotherm temperature and shorter dough and set times compared to comparative example 1. Further, example 6 displays similar dough times to comparative example 2, but has a longer set time, thereby giving a longer working time to administer the hardenable composition before it sets solid. Example 6 also has a lower exotherm temperature than comparative example 2.

TABLE 1

| Example number | Identity and weight of polymer component | Dry weight of polymer (g) | Dough time mins:secs | Set time mins:secs | Exotherm temperature (° C.) |
|---|---|---|---|---|---|
| 6 | Example 5, 17.2 g | 14.0 | 3:10 | 11:50 | 83.0 |
| Comp. Ex. 1 | Colacryl® B866, 14.0 g | 14.0 | 10:30 | 18:40 | 92.2 |
| Comp. Ex. 2 | Blend of Colacryl® B866 and spray dried emulsion of example 2, 86/14% wt, 14.0 g | 14.0 | 2:50 | 10:00 | 96.0 |

Examples 7 to 12

Preparation of Liquid First Part Using 50% wt Solids Acrylic Polymer Emulsion

To a 250 ml polypropylene beaker equipped with electric stirrer motor and stainless steel paddle stirrer is added poly(methyl methacrylate) (PMMA) bead polymer (Colacryl® B866, obtained from Lucite International Speciality Polymers & Resins Limited with R V of 2.4 dl/g, Mw 421,200, residual dibenzoyl peroxide 2.94% wt, mean particle size 39 microns). Stirring is commenced at 100 rpm and 50% wt solids acrylic polymer emulsion from example 3 is added over 60 to 90 seconds. The stirrer speed is then increased to 800-1000 rpm and mixing is continued for a further 3 to 5 minutes until a uniform liquid mixture is obtained. The amounts of PMMA bead polymer and acrylic polymer emulsion used in each example are shown in table 3, along with the Brookfield viscosity of each liquid mixture. All the liquid mixtures are stable with no separation after storage at 23° C. for several days.

TABLE 2

| Ex. | PMMA bead polymer (Colacryl® B866) (g) | 50% wt solids acrylic polymer emulsion from example 3 (g) | Brookfield Viscosity (cPs) |
|---|---|---|---|
| 7 | 55 | 45 | 4,200 |
| 8 | 65 | 35 | 5,720 |
| 9 | 70 | 30 | >90,000 |
| 10 | 75 | 25 | >90,000 |
| 11 | 80 | 20 | >90,000 |
| 12 | 82.5 | 17.5 | >90,000 |

Examples 13 to 18

Preparation of Hardenable Compositions

Hardenable compositions are prepared by mixing the liquids first part of examples 7 to 12 with MMA monomer containing 60 ppm hydroquinone (HQ) inhibitor and 1% N,N-dimethyl-para-toluidine (DMPT) accelerator (liquid second part). The mix ratio used is 14.0 g polymer (equivalent dry weight) to 7.0 ml monomer liquid. Before mixing, the two components are equilibrated for at least 10 hours in an incubator at 23° C. The required amount of liquid first part is placed into a polypropylene beaker, followed by the liquid second part. Timing is started from the point of adding the liquid second part to the liquid first part. Hand mixing is then carried out for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass. Table 3 records the results.

It can be seen that the exotherm temperature, dough time and set time all decrease as the amount of acrylic polymer emulsion increases in the order of example 18 to 13. Further, examples 13 to 18 display lower exotherm temperatures and shorter dough and set times compared to comparative example 1, demonstrating the benefits of the invention over the prior art.

TABLE 3

| Ex. | Identity and weight of polymer component | Dry weight of polymer (g) | Dough time mins:secs | Set time mins:secs | Exotherm temperature (° C.) |
|---|---|---|---|---|---|
| 13 | Example 7, 17.9 g | 14.0 | 1:15 | 9:00 | 75.4 |
| 14 | Example 8, 16.9 g | 14.0 | 1:25 | 9:30 | 76.0 |
| 15 | Example 9, 16.5 g | 14.0 | 1:35 | 10:50 | 79.5 |
| 16 | Example 10, 16.0 g | 14.0 | 3:00 | 11:00 | 82.8 |
| 17 | Example 11, 15.6 g | 14.0 | 3:20 | 11:00 | 89.7 |
| 18 | Example 12, 15.1 g | 14.0 | 3:30 | 11:30 | 91.2 |

Example 19

Preparation of Liquid First Part Using 54% wt Solids Acrylic Polymer Emulsion

To a 250 ml polypropylene beaker equipped with electric stirrer motor and stainless steel paddle stirrer is added 65 g of poly(methyl methacrylate) (PMMA) bead polymer (Colacryl® B866, obtained from Lucite International Speciality Polymers & Resins Limited with RV of 2.4 dl/g, Mw 421,200, residual dibenzoyl peroxide 2.94% wt, mean particle size 39 microns). Stirring is commenced at 100 rpm and 35 g of 54% wt solids acrylic polymer emulsion from example 4 is added over 60 to 90 seconds. The stirrer speed is then increased to 800-1000 rpm and mixing is continued for a further 3 to 5 minutes until a uniform liquid mixture is obtained. The liquid mixture is stable with no separation after storage at 23° C. for several days.

Example 20

Preparation of Hardenable Composition

A hardenable composition is prepared by mixing 16.7 g of the liquid first part of example 19 with 7 ml of MMA monomer containing 60 ppm hydroquinone (HQ) inhibitor and 1% N,N-dimethyl-para-toluidine (DMPT) accelerator (liquid second part). The mix ratio used is 14 g polymer (equivalent dry weight) to 7 ml monomer liquid. Before mixing, the two components are equilibrated for at least 10 hours in an incubator at 23° C. The required amount of liquid first part is placed into a polypropylene beaker, followed by the liquid second part. Timing is started from the point of adding the liquid second part to the liquid first part. Hand mixing is then carried out for 30 seconds using a metal spatula, whereupon the material is covered and left to stand.

Periodically, the material is assessed for initial mix consistency and the dough and set times determined. The exotherm temperature is also measured by use of a thermocouple embedded in the middle of the curing mass. Table 4 records the results.

TABLE 4

| Ex. | Identity and weight of polymer component | Dry weight of polymer (g) | Dough time mins:secs | Set time mins:secs | Exotherm temperature (° C.) |
|---|---|---|---|---|---|
| 20 | Example 19, 16.7 g | 14 | 1:00 | 10:00 | 80.8 |

It can be seen that example 20 displays a lower exotherm temperature and shorter dough and set times compared to comparative example 1.

Examples 21 and 22

Preparation of Hardenable Compositions Using a Liquid Second Part Containing Dissolved Polymer A 10% wt syrup of PMMA homopolymer in MMA monomer is prepared by dissolving 10 g of a PMMA bead polymer (free of residual initiator and with molecular weight Mw 426,700 daltons and reduced viscosity of 2.8 dl/g) in a mixture of 89 g of MMA monomer (stabilised with 60 ppm hydroquinone (HQ) inhibitor) and 1.0 g of N,N-dimethyl-para-toluidine (DMPT) accelerator. The Brookfield viscosity of the syrup is 220 cP.

Hardenable compositions are prepared by mixing the liquids first part of examples 7 and 8 with this liquid second part. The mix ratio used is 14.0 g polymer (equivalent dry weight) in the liquid first part to 7.0 g liquid second part. Before mixing, the components are equilibrated for at least 10 hours in an incubator at 23° C. The required amount of liquid first part is placed into a polypropylene beaker, followed by the liquid second part. Timing is started from the point of adding the liquid second part to the liquid first part. Hand mixing is then carried out for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass. Table 5 records the results.

TABLE 5

| Ex. | Identity and weight of polymer component | Dry weight of polymer (g) | Dough time mins:secs | Set time mins:secs | Exotherm temperature (° C.) |
|---|---|---|---|---|---|
| 21 | Example 7, 17.9 g | 14.0 | 0:20 | 8:30 | 67.4 |
| 22 | Example 8, 16.9 g | 14.0 | 0:25 | 10:15 | 74.4 |

It can be seen that examples 21 and 22 display much lower exotherm temperature and shorter dough and set times compared to comparative example 1. The effect of pre-dissolving some PMMA into the MMA monomer liquid to form a syrup as liquid second part is to produce a further lowering of the exotherm temperature and shortening of the dough and set times compared to the equivalent example without any PMMA pre-dissolved in the MMA monomer liquid, examples 13 and 14.

Examples 23 to 41

Preparation of Hardenable Compositions with Varying Mechanical Properties

The following examples show the effect of varying the composition of the liquid first part and the ratio of liquid first part to liquid second part on the mechanical properties of the resultant hardenable compositions. Flexural strength and flexural modulus were determined by a three-point bend test according to ISO 1567:1997. Compressive strength was determined according to ISO 5833:2002.

The liquids first part of examples 23 to 41 were prepared in a similar manner to examples 10 to 12, except for the examples involving addition of barium sulphate. For these particular examples (examples 30, 38 and 39), the required amount of barium sulphate is added to the mixture containing PMMA bead polymer and acrylic polymer emulsion over 60-90 seconds with stirring at 100 rpm, prior to increasing the stirrer speed to 800-1000 rom and mixing for a further 3 to 5 minutes before a uniform liquid mixture is obtained. The 16% wt syrup of PMMA homopolymer in MMA monomer used as the liquid second part of examples 23 to 41, except for examples 31, 32, 39 and 40, is prepared by dissolving 16 g of a PMMA bead polymer (free of residual initiator and with molecular weight Mw 426,700 daltons and reduced viscosity of 2.8 dl/g) in a mixture of 82.4 g of MMA monomer (stabilised with 60 ppm hydroquinone (HQ) inhibitor) and 1.6 g of N,N-dimethyl-para-toluidine (DMPT) accelerator. The Brookfield viscosity of the syrup is 4,250 cP.

The 20% wt syrups of poly(MMA-co-DMAEMA) copolymers in MMA monomer used as the liquid second part of examples 31, 32, 39 and 40 are prepared by dissolving 20 g of a poly(MMA-co-DMAEMA) copolymer (free of residual initiator) in a mixture of 78.4 g of MMA monomer (stabilised with 60 ppm hydroquinone (HQ) inhibitor) and 1.6 g of N,N-dimethyl-para-toluidine (DMPT) accelerator. For examples 31 and 39, the copolymer has a reduced viscosity of 0.50 dl/g and molecular weight Mw 69,900 daltons. The Brookfield viscosity of the syrup is 175 cP. For examples 32 and 40, the copolymer has a reduced viscosity of 1.52 dl/g and molecular weight Mw 260,000 daltons. The Brookfield viscosity of the syrup is 4,420 cP.

The liquid second parts of examples 40 and 41 include the addition of barium sulphate. These are prepared by firstly dissolving the relevant PMMA homopolymer or poly(MMA-co-DMAEMA) copolymer in MMA monomer (stabilised with 60 ppm hydroquinone (HQ) inhibitor) and N,N-dimethyl-para-toluidine (DMPT) accelerator in a glass flask equipped with stirrer. The required amount of barium sulphate is then added with stirring at 500-600 rpm and left for 1 hour to disperse the barium sulphate in the monomer/polymer syrup.

The hardenable compositions of examples 23 to 41 are prepared by mixing the two components by hand, as described for examples 21 and 22. The mix ratios used are either 14.0 g polymer (equivalent dry weight) in liquid first part to 7.0 g liquid second part or 14.0 g polymer (equivalent dry weight) in liquid first part to 14.0 g liquid second part.

Table 6 provides details on the composition of each component, the mix ratios used and the mechanical properties obtained from each hardenable composition. It can be seen that the magnitude of mechanical properties for examples 23 to 28 varies with the relative amount of acrylic polymer emulsion used. This stems from the presence of the water in the acrylic polymer emulsion which leads to the creation of porosity in the final cured hardenable composition. Increased porosity through increasing the proportion of acrylic polymer emulsion leads to reduction in mechanical properties in comparison to comparative example 3 which contains no added water. This porosity allows the mechanical properties of the hardenable composition to be matched to those of e.g. vertebral bone, thereby avoiding well known problems associated through implantation of artificial materials that are higher in modulus than the surrounding natural bone. However, the formulation can be also altered to adjust the level of porosity and vary the mechanical properties, e.g. to achieve mechanical properties that satisfy the requirements of ISO 5833:2002.

TABLE 6

|  | Composition of liquid first part | Composition of liquid second part | Ratio of liquid first part:liquid second part | Flexural strength (MPa) | Flexural Modulus (GPa) | Compressive Strength (MPa) |
| --- | --- | --- | --- | --- | --- | --- |
| Example 23 | Mixture of PMMA bead polymer (Colacryl ® B866), 82.5 g and 50% solids PMMA emulsion of example 3, 17.5 g. | 16% syrup of PMMA in MMA monomer containing 60 ppm HQ and 1.6% N,N-dimethyl-para-toluidine (DMPT) | 14.0 g:14.0 g | 84.1 | 2.54 | 99.9 |
| Example 24 | Mixture of PMMA bead polymer (Colacryl ® B866), 82.5 g and 50% solids PMMA emulsion of example 3, 17.5 g. | 16% syrup of PMMA in MMA monomer containing 60 ppm HQ and 1.6% N,N-dimethyl-para-toluidine (DMPT) | 14.0 g:7.0 g | 73.4 | 2.56 | 104 |
| Example 25 | Mixture of PMMA bead polymer (Colacryl ® B866), 80.0 g and 50% solids PMMA emulsion of example 3, 20.0 g. | 16% syrup of PMMA in MMA monomer containing 60 ppm HQ and 1.6% N,N-dimethyl-para-toluidine (DMPT) | 14.0 g:14.0 g | 70.8 | 2.42 | 95.4 |
| Example 26 | Mixture of PMMA bead polymer (Colacryl ® B866), 80.0 g and 50% solids PMMA emulsion of example 3, 20.0 g. | 16% syrup of PMMA in MMA monomer containing 60 ppm HQ and 1.6% N,N-dimethyl-para-toluidine (DMPT) | 14.0 g:7.0 g | 66.7 | 2.20 | 89.0 |
| Example 27 | Mixture of PMMA bead polymer (Colacryl ® B866), 75.0 g and 50% solids PMMA emulsion of example 3, 25.0 g. | 16% syrup of PMMA in MMA monomer containing 60 ppm HQ and 1.6% N,N-dimethyl-para-toluidine (DMPT) | 14.0 g:14.0 g | 71.4 | 2.45 | 91.0 |
| Example 28 | Mixture of PMMA bead polymer (Colacryl ® B866), 75.0 g and 50% solids PMMA emulsion of example 3, 25.0 g. | 16% syrup of PMMA in MMA monomer containing 60 ppm HQ and 1.6% N,N-dimethyl-para-toluidine (DMPT) | 14.0 g:7.0 g | 70.7 | 2.35 | 86.6 |
| Example 29 | 50% solids PMMA emulsion of example 3 (no PMMA bead polymer). | 16% syrup of PMMA in MMA monomer containing 60 ppm HQ and 1.6% N,N-dimethyl-para-toluidine (DMPT) | 14.0 g:14.0 g | 24.3 | 1.33 | 50.4 |
| Example 30 | Mixture of 50% solids PMMA emulsion of example 3, 60.0 g and barium sulphate, 40.0 g. | 16% syrup of PMMA in MMA monomer containing 60 ppm HQ and 1.6% N,N-dimethyl-para-toluidine (DMPT) | 14.0 g:14.0 g The amount of barium sulphate in the cured composition is 20 w/w % | 39.6 | 2.10 | 51.5 |
| Example 31 | Mixture of PMMA bead polymer (Colacryl ® B866), 75.0 g and 50% solids PMMA emulsion of example 3, 25.0 g. | 20% syrup of poly(MMA-co-DMAEMA) (RV = 0.5) in MMA monomer containing 60 ppm HQ and 1.0% N,N-dimethyl-para-toluidine (DMPT) | 14.0 g:14.0 g | 71.4 | 2.45 | 92.5 |

TABLE 6-continued

|  | Composition of liquid first part | Composition of liquid second part | Ratio of liquid first part:liquid second part | Flexural strength (MPa) | Flexural Modulus (GPa) | Compressive Strength (MPa) |
|---|---|---|---|---|---|---|
| Example 32 | Mixture of PMMA bead polymer (Colacryl ® B866), 75.0 g and 50% solids PMMA emulsion of example 3, 25.0 g. | 20% syrup of poly(MMA-co-DMAEMA) (RV = 1.52) in MMA monomer containing 60 ppm HQ and 1.0% N,N-dimethyl-para-toluidine (DMPT) | 14.0 g:14.0 g | 69.3 | 2.30 | 99.6 |
| Example 33 | Mixture of PMMA bead polymer (Colacryl ® B866), 82.5 g and 50% solids PMMA emulsion of example 3, 17.5 g. | 16% syrup of PMMA in MMA monomer containing 60 ppm HQ and 1.6% N,N-dimethyl-para-toluidine (DMPT) | 14.0 g:14.0 g | 84.1 | 2.54 | 109 |
| Example 34 | Mixture of PMMA bead polymer (Colacryl ® B866), 70.0 g and 50% solids PMMA emulsion of example 3, 30.0 g. | 16% syrup of PMMA in MMA monomer containing 60 ppm HQ and 1.6% N,N-dimethyl-para-toluidine (DMPT) | 14.0 g:14.0 g | 68.7 | 2.79 | 83.4 |
| Example 35 | Mixture of PMMA bead polymer (Colacryl ® B866), 65.0 g and 50% solids PMMA emulsion of example 3, 35.0 g. | 16% syrup of PMMA in MMA monomer containing 60 ppm HQ and 1.6% N,N-dimethyl-para-toluidine (DMPT) | 14.0 g:14.0 g | 62.67 | 2.23 | 76.0 |
| Example 36 | Mixture of PMMA bead polymer (Colacryl ® B866), 60.0 g and 50% solids PMMA emulsion of example 3, 40.0 g. | 16% syrup of PMMA in MMA monomer containing 60 ppm HQ and 1.6% N,N-dimethyl-para-toluidine (DMPT) | 14.0 g:14.0 g | 54.9 | 2.07 | 72.7 |
| Example 37 | Mixture of poly(MMA-co-styrene) bead copolymer (Colacryl ® TS1260), 70.0 g and 50% solids PMMA emulsion of example 3, 30.0 g. | 16% syrup of PMMA in MMA monomer containing 60 ppm HQ and 1.6% N,N-dimethyl-para-toluidine (DMPT) | 14.0 g:14.0 g | 61.2 | 2.14 | 80.1 |
| Example 38 | Mixture of PMMA bead polymer (Colacryl ® B866), 35.0 g, 50% solids PMMA emulsion of example 3, 25.0 g and barium sulphate, 40.0 g. | 16% syrup of PMMA in MMA monomer containing 60 ppm HQ and 1.6% N,N-dimethyl-para-toluidine (DMPT) | 14.0 g: 14.0 g The amount of barium sulphate in the cured composition is 20 w/w % | 46.5 | 2.16 | 74.1 |
| Example 39 | Mixture of PMMA bead polymer (Colacryl ® B866), 35.0 g, 50% solids PMMA emulsion of example 3, 25.0 g and Barium sulfate 40.0 g. | 20% syrup of poly(MMA-co-DMAEMA) (RV = 0.5) in MMA monomer containing 60 ppm HQ and 1.0% N,N-dimethyl-para-toluidine (DMPT) | 14.0 g:14.0 g The amount of barium sulphate in the cured composition is 20 w/w % | 45.1 | 2.50 | 74.7 |
| Example 40 | Mixture of PMMA bead polymer (Colacryl ® B866), 75.0 g and 50% solids PMMA emulsion of example 3, 25.0 g. | Mixture consisting of 12.0 g of 20% syrup of poly(MMA-co-DMAEMA) (RV = 1.52) in MMA monomer containing 60 ppm HQ and 1.0% N,N-dimethyl-para-toluidine | 14.0 g:14.0 g The amount of barium sulphate in the cured composition is 20 w/w % | 47.4 | 2.45 | 77.0 |

TABLE 6-continued

|  | Composition of liquid first part | Composition of liquid second part | Ratio of liquid first part:liquid second part | Flexural strength (MPa) | Flexural Modulus (GPa) | Compressive Strength (MPa) |
|---|---|---|---|---|---|---|
| Example 41 | Mixture of PMMA bead polymer (Colacryl ® B866), 75.0 g and 50% solids PMMA emulsion of example 3, 25.0 g. | (DMPT) with 8.0 g of barium sulphate Mixture consisting of 12.0 g of 16% syrup of PMMA in MMA monomer containing 60 ppm HQ and 1.6% N,N-dimethyl-para-toluidine (DMPT) with 8.0 g barium sulfate | 14.0 g: 14.0 g The amount of barium sulphate in the cured composition is 20 w/w % | 45.1 | 2.50 | 78.7 |

Examples 42 to 45 describe the preparation of acrylic emulsions of 50% wt solids and varying z-average particle size.

Example 42

Preparation of ca. 50% wt Solids Acrylic Polymer Emulsion of 195 nm z-Average Particle Size 600 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 1000 grams methyl methacrylate, 0.5 grams of 1-dodecanethiol, 5.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) is prepared by adding 100 grams of the emulsified monomer mixture to the flask followed by 10 milliliters of a 2 wt % solution of potassium persulphate in deionised water. Following a slight exotherm the reaction proceeds for thirty minutes until the temperature returns to 80° C. To the remaining emulsified monomer mixture is added 1 g of sodium lauryl sulphate with stirring.

The core is then grown over the polymer seed particles (Stage 2) by firstly adding 10 milliliters of a 2 wt % solution of potassium persulphate in deionised water to the flask followed by continuous addition of 300 grams of the emulsified monomer mixture over approximately 30 minutes using a peristaltic pump. The reaction proceeds for a further 15 minutes after the completion of addition of the monomer mixture until the temperature returns to 80° C. This step is then repeated twice.

35.0 grams of 75% active dibenzoyl peroxide (BPO) are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 20 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The resultant acrylic polymer emulsion has a solids content of 50% wt, reduced viscosity of 2.3 dl/g, Brookfield Viscosity of 287 cPs, residual dibenzoyl peroxide of 2.50% wt and a z-average emulsion particle size of 195 nm.

Example 43

Preparation of ca. 50% wt Solids Acrylic Polymer Emulsion of 306 nm z-Average Particle Size 600 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 1000 grams methyl methacrylate, 0.5 grams of 1-dodecanethiol, 5.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) is prepared by adding 40 grams of the emulsified monomer mixture to the flask followed by 20 milliliters of a 2 wt % solution of potassium persulphate in deionised water. Following a slight exotherm the reaction proceeds for thirty minutes until the temperature returns to 80° C.

The core is then grown over the polymer seed particles (Stage 2) by firstly adding 10 milliliters of a 2 wt % solution of potassium persulphate in deionised water to the flask followed by continuous addition of 300 grams of the emulsified monomer mixture over approximately 30 minutes using a peristaltic pump. The reaction proceeds for a further 15 minutes after the completion of addition of the monomer mixture until the temperature returns to 80° C. This step is then repeated twice.

35.0 grams of 75% active dibenzoyl peroxide (BPO) are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 20 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The resultant acrylic polymer emulsion has a solids content of 49.4% wt, reduced viscosity of 2.0 dl/g, Brookfield Viscosity of 62 cPs, residual dibenzoyl peroxide of 2.30% wt and a z-average emulsion particle size of 306 nm.

Example 44

Preparation of ca. 50% wt Solids Acrylic Polymer Emulsion of 582 nm z-Average Particle Size 600 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 980 grams methyl methacrylate, 0.5 grams of 1-dodecanethiol, 5.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) is prepared by adding 20 grams of methyl methacrylate to the flask followed by a solution of 0.3 grams potassium persulphate in 10 milliliters of deionised water and react at 80° C. for 1 hour.

The core is then grown over the polymer seed particles (Stage 2) by firstly adding 10 milliliters of a 2 wt % solution of potassium persulphate in deionised water to the flask followed by continuous addition of 300 grams of the emulsified monomer mixture over approximately 30 minutes using a peristaltic pump. The reaction proceeds for a further 15 minutes after the completion of addition of the monomer mixture until the temperature returns to 80° C. This step is then repeated twice.

35.0 grams of 75% active dibenzoyl peroxide (BPO) are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 20 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The resultant acrylic polymer emulsion has a solids content of 48.0% wt, reduced viscosity of 1.94 dl/g, Brookfield Viscosity of 21 cPs, residual dibenzoyl peroxide of 2.28% wt and a z-average emulsion particle size of 582 nm.

Example 45

Preparation of ca. 50% wt Solids Acrylic Polymer Emulsion of 694 nm z-average Particle Size 600 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid.

An emulsified monomer mixture is prepared consisting of 985 grams methyl methacrylate, 0.5 grams of 1-dodecanethiol, 3.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) is prepared by adding 15 grams of methyl methacrylate to the flask followed by a solution of 0.3 grams potassium persulphate in 10 milliliters of deionised water and react at 80° C. for 1 hour.

The core is then grown over the polymer seed particles (Stage 2) by firstly adding 10 milliliters of a 2 wt % solution of potassium persulphate in deionised water to the flask followed by continuous addition of 300 grams of the emulsified monomer mixture over approximately 30 minutes using a peristaltic pump. The reaction proceeds for a further 15 minutes after the completion of addition of the monomer mixture until the temperature returns to 80° C. This step is then repeated twice.

35.0 grams of 75% active dibenzoyl peroxide (BPO) are dissolved in the remaining emulsified monomer mixture with stirring for 45 minutes.

The BPO-containing shell is then grown over the core (Stage 3) by firstly adding 10 milliliters of a 2 wt % solution of potassium persulphate in deionised water to the flask followed by continuous addition of the emulsified monomer mixture containing added BPO over approximately 20 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 micron screen.

The resultant acrylic polymer emulsion has a solids content of 48.0% wt, reduced viscosity of 1.90 dl/g, Brookfield Viscosity of 19 cPs, residual dibenzoyl peroxide of 2.60% wt and a z-average emulsion particle size of 694 nm.

Example 46

The results of examples 42 to 45 show that the Brookfield viscosity of the acrylic polymer emulsions reduces as the particle size increases. An acrylic polymer emulsion mixture was prepared by taking equal amounts (100 g each) of the emulsions of examples 42 to 44. The Brookfield viscosity was 40 cPs. Table 7 shows the viscosity comparison between the single emulsions of examples 42, 43 and 44 with the mixture of emulsions, example 46.

TABLE 7

| Example | Solids content (% wt) | Z-average particle size (nm) | Brookfield viscosity (cPs) |
|---|---|---|---|
| 42 | 50.0 | 195 | 287 |
| 43 | 49.4 | 306 | 62 |

TABLE 7-continued

| Example | Solids content (% wt) | Z-average particle size (nm) | Brookfield viscosity (cPs) |
|---|---|---|---|
| 44 | 48.0 | 582 | 21 |
| 46 | 49.1 | Mixture of examples 42, 43 and 44 (equal amounts) | 40 |

Examples 47 to 65

Examples 47 to 65 involve the preparation of the liquid first part by mixing the acrylic polymer emulsions of examples 42, 43, 44 or 46 with either single acrylic bead polymers (examples 48 to 50, 52 to 54 and 56 to 58) or mixtures of acrylic bead polymers (examples 47, 51, 55 and 59 to 65). The acrylic bead polymers (described in detail in table 8) are selected from either PMMA homopolymers of different mean diameter particle size (designated (i), (ii) and (iii)) or copolymers, i.e. poly(methyl methacrylate-co-2-ethylhexyl acrylate) (poly(MMA-co-2EHA)) (designated (iv), (v), and (vi)) and poly(methyl methacrylate-co-styrene) (poly(MMA-co-sty) (designated (vii), (viii) and (ix)). The preparation method for the liquid first part of examples 47 to 61 is as follows:

To a 250 ml polypropylene beaker equipped with electric stirrer motor and stainless steel paddle stirrer is added 70 g of acrylic bead polymer. Stirring is commenced at 100 rpm and 30 g of acrylic polymer emulsion is added over 60 to 90 seconds. The stirrer speed is then increased to 600-1000 rpm and mixing is continued for a further 3 to 5 minutes until a uniform liquid mixture is obtained. If a mixture of acrylic bead polymers is used, the mixture is firstly prepared by dry blending equal weights of each bead polymer in a suitable container.

The same preparation method is used for examples 62 to 65 except that the ratio of acrylic bead polymer to acrylic polymer emulsion is varied from 70 g:30 g to 76 g:24 g.

After preparation, the Brookfield viscosity of each liquid first part was measured and recorded in tables 9 to 14.

An assessment of mixing and dispensing behaviour through a static mixer connected to compartments of a syringe or caulking gun was carried out as follows. The liquid first parts of examples 47 to 65 and the liquid second part of example 78 were filled into separate compartments of a 50 ml 1:1 vol:vol polypropylene cartridge available from Nordson EFD. A Nordson EFD Series 190 spiral mixer (11 mixing elements, 6.35 mm diameter, 8.6 cm length) was fitted to the twin compartments of the cartridge and the contents were dispensed as a homogeneous stream through the spiral mixer onto a flat surface for examination. The extent of flow of each mixture through the static mixer from entrance to exit was recorded. The characteristics of the resulting extrudate were also assessed and it was found that in all examples of continuous flow the extrudate retained its original shape. The results are reported in tables 9 to 14.

The results of tables 9 to 14 show how the Brookfield viscosities of the liquid first part can be reduced. The following observations can be made:

1. Comparison of example 47 with examples 48 to 50, or example 51 with examples 52 to 54 or example 55 with examples 56 to 58 show that a liquid first part prepared by mixing an acrylic polymer emulsion with a mixture of acrylic bead polymers displays a lower Brookfield viscosity than a liquid first part containing a single type of acrylic bead polymer.
2. Comparison of examples 47, 51 and 55 shows that the Brookfield viscosity of the liquid first part reduces as the particle size of the acrylic polymer emulsion increases.
3. Example 61 shows that the liquid first part prepared by combining a mixture of acrylic polymer emulsions with a mixture of acrylic bead polymers displays a lower Brookfield viscosity than the liquid first part of examples 47 and 51.

Examples 62 to 65 (table 14) show how the Brookfield viscosity of a liquid first part increases as the ratio of acrylic bead to acrylic polymer emulsion increases.

TABLE 8

Acrylic bead polymers used in examples 47 to 65

| Monomer identity and copolymer composition | Reference number | Reduced Viscosity (dl/g) | Molecular weight (Mw) | Residual dibenzoyl peroxide (% wt) | Mean diameter particle size (microns) |
|---|---|---|---|---|---|
| PMMA homopolymer | (i) | 2.29 | 414,150 | 2.83 | 42 |
| PMMA homopolymer | (ii) | 6.62 | 686,390 | 0.23 | 89 |
| PMMA homopolymer | (iii) | 7.05 | 724,680 | 0.24 | 156 |
| Poly(MMA-co-2EHA) 92:8% wt | (iv) | 2.00 | 442,140 | 1.16 | 28 |
| Poly(MMA-co-2EHA) 92:8% wt | (v) | 2.14 | 409,420 | 1.19 | 78 |
| Poly(MMA-co-2EHA) 92:8% wt | (vi) | 1.81 | 327,960 | 1.42 | 147 |
| Poly(MMA-co-sty) 96:4% wt | (vii) | 1.37 | 257,800 | 2.52 | 35 |
| Poly(MMA-co-sty) 92.5/7.5% wt | (viii) | 1.08 | 180,110 | 2.48 | 112 |
| Poly(MMA-co-sty) 92.5/7.5% wt | (ix) | 1.10 | 160,320 | 2.60 | 138 |

TABLE 9

Liquid first part prepared from PMMA beads and acrylic polymer emulsion of example 42

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 47 | PMMA bead mixture - equal parts of (i), (ii) and (iii) 42, 89, 156 microns | 70 | Example 42: 195 nm | 30 | 20,250 | 3 |
| 48 | PMMA (i), 42 microns | 70 | Example 42: 195 nm | 30 | >90,000 | 1 |

TABLE 9-continued

Liquid first part prepared from PMMA beads and acrylic polymer emulsion of example 42

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 49 | PMMA (ii), 89 microns | 70 | Example 42: 195 nm | 30 | >90,000 | 1 |
| 50 | PMMA (iii), 156 microns | 70 | Example 42: 195 nm | 30 | >90,000 | 1 |

TABLE 10

Liquid first part prepared from PMMA beads and acrylic polymer emulsion of example 43

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 51 | PMMA bead mixture - equal parts of (i), (ii) and (iii) 42, 89, 156 microns | 70 | Example 43: 306 nm | 30 | 3,600 | Continuous flow: - 8.6+ |
| 52 | PMMA (i), 42 microns | 70 | Example 43: 306 nm | 30 | >90,000 | 1 |
| 53 | PMMA (ii), 89 microns | 70 | Example 43: 306 nm | 30 | >90,000 | 1 |
| 54 | PMMA (iii), 156 microns | 70 | Example 43: 306 nm | 30 | >90,000 | 1 |

TABLE 11

Liquid first part prepared from PMMA beads and acrylic polymer emulsion of example 44

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 55 | PMMA bead mixture - equal parts of (i), (ii) and (iii) 42, 89, 156 microns | 70 | Example 44: 582 nm | 30 | 1,950 | Continuous flow: 8.6+ |
| 56 | PMMA (i), 42 microns | 70 | Example 44: 582 nm | 30 | 33,400 | 6 |
| 57 | PMMA (ii), 89 microns | 70 | Example 44: 582 nm | 30 | 22,700 | 3 |
| 58 | PMMA (iii), 156 microns | 70 | Example 44: 582 nm | 30 | 9,500 | 4 |

TABLE 12

Liquid first part prepared from either poly(MMA-co-2EHA) bead mixture or poly(MMA-co-styrene) bead mixture and acrylic polymer emulsion of example 44

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 59 | Poly(MMA-co-2EHA) bead mixture - equal parts of (iv), (v) and (vi) 28, 78, 147 microns | 70 | Example 44: 582 nm | 30 | 3,700 | Continuous flow: 8.6+ |

TABLE 12-continued

Liquid first part prepared from either poly(MMA-co-2EHA) bead mixture or poly(MMA-co-styrene) bead mixture and acrylic polymer emulsion of example 44

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 60 | Poly(MMA-co-sty) bead mixture - equal parts of (vii), (viii) and (ix) 35, 112, 138 microns | 70 | Example 44: 582 nm | 30 | 2,250 | Continuous flow: 8.6+ |

TABLE 13

Liquid first part prepared from PMMA bead mixture and acrylic polymer emulsion mixture of example 46

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 61 | PMMA bead mixture - equal parts of (i), (ii) and (iii) 42, 89, 156 microns | 70 | Emulsion mixture from example 46 | 30 | 3,350 | Continuous flow: 8.6+ |

TABLE 14

Liquid first part prepared with varying ratio of PMMA bead mixture to acrylic polymer emulsion

| Example Number | Acrylic bead polymer identity | Acrylic bead polymer weight (grams) | Acrylic polymer emulsion identity and Z-average particle size | Acrylic polymer emulsion weight (grams) | Brookfield viscosity (cPs) | Extent of flow through static mixer (cm) |
|---|---|---|---|---|---|---|
| 62 | PMMA bead mixture - equal parts of (i), (ii) and (iii) 42, 89, 156 microns | 70 | Example 44: 582 nm | 30 | 1,950 | Continuous flow: 8.6+ |
| 63 | PMMA bead mixture - equal parts of (i), (ii) and (iii) 42, 89, 156 microns | 72 | Example 44: 582 nm | 28 | 4,020 | Continuous flow: 8.6+ |
| 64 | PMMA bead mixture - equal parts of (i), (ii) and (iii) 42, 89, 156 microns | 74 | Example 44: 582 nm | 26 | 28,020 | 4 |
| 65 | PMMA bead mixture - equal parts of (i), (ii) and (iii) 42, 89, 156 microns | 76 | Example 44: 582 nm | 24 | 54,000 | 2 |

TABLE 15

Brookfield viscosity of liquid first part prepared from acrylic polymer emulsion of example 44 and different mixtures of acrylic bead polymers

| | Acrylic bead polymer identity and ratio (% wt) | | | |
|---|---|---|---|---|
| Example Number | PMMA homopolymer (i) 42 microns | PMMA homopolymer (ii) 89 microns | PMMA homopolymer (iii) 156 microns | Brookfield viscosity (cPs) |
| 66 | 50 | 50 | 0 | 2,200 |
| 67 | 50 | 0 | 50 | 550 |
| 68 | 40 | 25 | 25 | 1,120 |

TABLE 15-continued

Brookfield viscosity of liquid first part prepared from acrylic polymer emulsion of example 44 and different mixtures of acrylic bead polymers

| 69 | 35 | 35 | 35 | 1,950 |
| 70 | 25 | 35 | 40 | 1,930 |
| 71 | 25 | 40 | 35 | 1,850 |
| 72 | 0  | 50 | 50 | 8,700 |

| | Poly(MMA-co-2EHA) 92:8% wt (iv) 28 microns | Poly(MMA-co-2EHA) 92:8% wt (v) 78 microns | Poly(MMA-co-2EHA) 92:8% wt (vi) 147 microns | |
|---|---|---|---|---|
| 73 | 50 | 0  | 50 | 1,800 |
| 74 | 40 | 25 | 35 | 2,400 |
| 75 | 35 | 35 | 35 | 3,700 |
| 76 | 25 | 35 | 40 | 6,600 |
| 77 | 25 | 40 | 35 | 7,300 |

Examples 66 to 77

These examples show the viscosity-reducing effect on a liquid first part obtained from mixing a given acrylic polymer emulsion with mixtures of different ratios of acrylic bead polymers of different particle sizes. The results are presented in table 15. Two series of experiments were carried out. One series was based on PMMA homopolymers of different mean diameter particle size (designated (i), (ii) and (iii)). A second series was based on poly(MMA-co-2EHA) copolymers of different mean diameter particle size (designated (iv), (v), and (vi)). The details on polymers (i) to (vi) are provided in table 8. The general preparation method for the each liquid first part is as follows:

To a 250 ml polypropylene beaker equipped with electric stirrer motor and stainless steel paddle stirrer is added 70 g of acrylic bead polymer mixture. The composition of the acrylic bead polymer mixture used for each example is detailed in table 15. Stirring is commenced at 100 rpm and 30 g of acrylic polymer emulsion of example 44 is added over 60 to 90 seconds. The stirrer speed is then increased to 600-1000 rpm and mixing is continued for a further 3 to 5 minutes until a uniform liquid mixture is obtained.

Comparison of examples 66 to 72 with examples 56 to 58 shows that the use of a mixture of two or more PMMA bead polymers of different mean diameter particle size produces a liquid first part that demonstrates a lower Brookfield viscosity than when only a single PMMA bead polymer is used. Examples 73 to 77 show that a similar viscosity-reducing effect is produced when using mixtures of two or more poly(MMA-co-2EHA) bead copolymers of different mean diameter particle size.

Example 78

Preparation of a Liquid Second Part Containing Dissolved Polymer and X-Ray Opacifier for Use in Making Hardenable Compositions The liquid second part is prepared as follows. Firstly, 10 g of a poly(MMA-co-DMAEMA) copolymer (free of residual initiator, RV=0.50 dl/g) and 10 g of a higher molecular weight poly(MMA-co-DMAEMA) copolymer (free of residual initiator, RV=1.52 dl/g) is dissolved in a mixture of 79.2 g of MMA monomer (stabilised with 60 ppm hydroquinone (HQ) inhibitor) and 0.8 g of N,N-dimethyl-para-toluidine (DMPT) accelerator. 60 g of this monomer/polymer syrup is then transferred to a glass flask equipped with stirrer and 40 g of barium sulphate is added slowly over two minutes with stirring at 500-600 rpm. Stirring is continued for 5 hours to disperse the barium sulphate in the monomer/polymer syrup. The Brookfield viscosity of the resultant liquid second part is 2,734 cPs.

Example 79

Preparation of a Hardenable Composition Using the Liquid First Part of Example 60 and the Liquid Second Part of Example 78

The preparation of a hardenable composition from combining the liquid first part of example 60 with the liquid second part of example 78 is described as follows. Before mixing, the two components are equilibrated for at least 10 hours in an incubator at 23° C. 14.0 g of the liquid first part of 60 is placed into a polypropylene beaker followed by 14.0 g of the liquid second part of example 78. Hand mixing is then carried out at 23° C. for 30 seconds using a metal spatula, whereupon the material is covered and left to stand. Periodically, the material is assessed for initial mix consistency. When the dough time is achieved, the doughed mixture is removed from the beaker and further mixed by hand manipulation for 30 seconds. For preparing specimens for mechanical testing, the dough is packed into metal moulds preconditioned at 23° C. and allowed to harden under pressure (2 bar). The specimens are demoulded 30 minutes after the set time. Table 16 records the results.

TABLE 16

Mechanical properties of hardenable composition prepared from mixing the liquid first part of example 60 with the liquid second part of example 78

| Example number | Composition of liquid first part | Flexural strength (MPa) | Flexural Modulus (GPa) | Compressive Strength (MPa) |
|---|---|---|---|---|
| 79 | Ex. 60: Poly(MMA-co-sty) bead mixture - equal parts of (vii), (viii) and (ix) 35, 112, 138 microns: PMMA emulsion of example 44 (blend ratio bead polymer:emulsion = 70:30% wt) | 50.5 | 2.16 | 73.1 |

It can be seen that the hardenable composition of example 79 displays mechanical properties that exceed the minimum requirements of ISO 5833:2002—"Implants for surgery—Acrylic resin cements", i.e. compressive strength ≥70 MPa, flexural modulus ≥1.8 GPa and flexural strength ≥50 MPa.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, wherein the said monomer component and the said initiator component are located in separate parts of the said two part composition so that the monomer component is storage stable wherein the liquid first part comprises emulsion polymerized acrylic polymer particles in a liquid carrier and initiator and the second part comprises acrylic monomer and accelerator.

2. A hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, wherein the liquid first part comprises emulsion polymerized acrylic polymer particles in a liquid carrier and initiator and the second part comprises acrylic monomer and accelerator.

3. A hardenable two part acrylic composition according to claim 1, wherein the emulsion polymerized particles in a liquid carrier are in the form of an acrylic polymer emulsion.

4. A hardenable two part acrylic composition according to claim 1, wherein the liquid carrier is water.

5. A hardenable two part acrylic composition according to claim 2 or 3, wherein the acrylic polymer emulsion provides a continuous phase for the liquid first part.

6. A hardenable two part acrylic composition according to claim 2, 3 or 4, wherein the acrylic polymer emulsion consists of emulsion polymerized acrylic polymer particles, at least one emulsifier and water.

7. A hardenable two part acrylic composition according to claim 1, wherein the two part acrylic composition also comprises at least one further type of acrylic polymer particles.

8. A hardenable two part acrylic composition according to claim 1, wherein at least one further type(s) of acrylic polymer particles are polymer beads.

9. A hardenable two part acrylic composition according to claim 1, wherein the polymerized emulsion particles and, if present, further types of polymer particles form at least 98% of the polymer present in the two part acrylic composition prior to mixing.

10. A hardenable two part acrylic composition according to claim 1, wherein the first part further comprises a second or further population of emulsion polymerized acrylic polymer particles and wherein the z-average particle size of the second or further populations of emulsion polymerized acrylic polymer particles is in the range 10-2,000 nm.

11. A method of reducing dough time for a hardenable two part acrylic composition comprising the steps of combining a liquid first part as defined in claim 1 with a liquid second part as defined in claim 1.

12. A solid cement composition produced from mixing a two part acrylic composition according to claim 1.

13. A process of producing an acrylic cement from a two part acrylic composition according to claim 1 by mixing the said first and second parts.

14. A syringe or caulking gun having at least two barrels comprising the liquid first part according to claim 1 in a first barrel thereof and a liquid second part according to claim 1 in the second barrel thereof.

15. A hardenable two part acrylic composition according to claim 1 adapted for use in the treatment of human or animal bone.

16. A hardenable two part acrylic composition according to claim 1, wherein the Brookfield viscosity range at 25° C. for the liquid first part and liquid second part are between 10 and 10,000 centipoise.

17. A hardenable two part acrylic composition according to claim 1, wherein the first part further comprises a second or further population of emulsion polymerised acrylic polymer particles having a different respective z-average particle size(s) from the emulsion polymerised acrylic polymer particles of claim 1.

18. A hardenable two part acrylic composition according to claim 1, wherein the z-average particle size of the emulsion polymerized acrylic polymer particles and/or the second or further populations of emulsion polymerised acrylic polymer particles are independently in the range 10-2,000 nm.

19. A hardenable two part acrylic composition according to claim 1, wherein the first part further comprises two or more further types of acrylic polymer particle populations said further types having different respective mean diameter particle sizes from each other.

20. A hardenable two part acrylic composition according to claim 7, wherein the mean diameter particle size of the further acrylic polymer particles is 10-1,000 microns.

21. A hardenable two part acrylic composition comprising a storage stable liquid first part and a storage stable liquid second part which react with each other upon mixing to form a cement which hardens, the composition further comprising an acrylic monomer component and an initiator component in an amount effective to polymerize the monomer component, wherein the liquid first part comprises in a liquid carrier a first population of emulsion polymerized acrylic polymer particles and a second population of emulsion polymerised acrylic polymer particles having different z-average particle size's from the first emulsion polymerised acrylic polymer particles.

22. A hardenable two part acrylic composition according to claim 2, wherein there are two or more further types of acrylic polymer particle populations, said further types having different respective mean diameter particle sizes from each other and wherein the liquid first part comprises in a liquid carrier a first population of emulsion polymerized acrylic polymer particles and the said two or more further types of acrylic polymer particle populations said further types having different respective mean diameter particle sizes from each other.

23. A method of producing a hardenable two part acrylic composition comprising a storage stable liquid first part and a storage stable liquid second part which react with each other upon mixing to form a cement which hardens to a solid, comprising the steps of: —
  (a) emulsion polymerizing an acrylic monomer composition in the presence of excess initiator to produce an acrylic polymer emulsion with residual initiator; or
  (b) emulsion polymerizing an acrylic monomer composition to produce an acrylic polymer emulsion and adding initiator to the emulsion; or
  (c) emulsion polymerizing an acrylic monomer composition to produce an acrylic polymer emulsion without excess initiator;
  (d) optionally, mixing the emulsion from (a) or (b) with at least one further type of acrylic polymer particles or mixing the emulsion from (c) with a solution of the said further type of acrylic polymer in acrylic monomer, to thereby produce a liquid acrylic polymer first part suitable for hardening at a predetermined rate in the joint presence of an acrylic monomer and initiator.

24. A liquid composition comprising emulsion polymerized acrylic polymer particles, optionally, mixed with at least one further type of non-emulsion polymerized acrylic particles, and wherein there is a polymerization initiator in the liquid composition at a level sufficient to cause the liquid composition to harden upon contact with a reactive monomer liquid.

25. A solid cement composition produced from mixing a two part acrylic composition according to any of claim 4, 7-10 or 15-20, wherein the cement is porous.

26. A solid cement composition according to claim 25, which is a bone cement and wherein the porosity including size and topography provides controlled release of antibiotics and other medicines into the surrounding bone and tissue.

27. A solid cement composition produced from mixing a two part acrylic composition according to claim 5, wherein the cement is porous.

28. A solid cement composition according to claim 27, which is a bone cement and wherein the porosity including size and topography provides controlled release of antibiotics and other medicines into the surrounding bone and tissue.

29. A solid cement composition produced from mixing a two part acrylic composition according to claim 6, wherein the cement is porous.

30. A solid cement composition according to claim 29, which is a bone cement and wherein the porosity including size and topography provides controlled release of antibiotics and other medicines into the surrounding bone and tissue.

* * * * *